United States Patent [19]
Bell et al.

[11] Patent Number: 5,786,356
[45] Date of Patent: Jul. 28, 1998

[54] SELECTIVE β3 ADRENERGIC AGONISTS

[75] Inventors: Michael Gregory Bell; Thomas Alan Crowell; Donald Paul Matthews, all of Indianapolis; John Hampton McDonald, III, Carmel; David Andrew Neel, Zionsville; Anthony John Shuker; Mark Alan Winter, both of Indianapolis, all of Ind.

[73] Assignee: Eli Lilly and Company, Indianapolis, Ind.

[21] Appl. No.: 882,549

[22] Filed: Jun. 25, 1997

Related U.S. Application Data

[62] Division of Ser. No. 708,621, Sep. 5, 1996, abandoned.

[51] Int. Cl.$^6$ .................... A61K 31/495; C07D 403/12
[52] U.S. Cl. ................................ 514/248; 544/237
[58] Field of Search ................ 544/237; 514/248

[56] References Cited

U.S. PATENT DOCUMENTS

| | | | |
|---|---|---|---|
| 4,032,575 | 6/1977 | Ikezaki et al. | 260/570.6 |
| 4,288,452 | 9/1981 | Sombroek et al. | 424/304 |
| 4,309,443 | 1/1982 | Smith et al. | 424/319 |
| 4,338,333 | 7/1982 | Ainsworth et al. | 424/309 |
| 4,346,093 | 8/1982 | Friebe et al. | 424/269 |
| 4,367,235 | 1/1983 | Ross et al. | 424/273 B |
| 4,385,066 | 5/1983 | Ainsworth et al. | 424/309 |
| 4,391,826 | 7/1983 | Mills et al. | 424/324 |
| 4,396,627 | 8/1983 | Ainsworth et al. | 424/309 |
| 4,432,993 | 2/1984 | Ferris | 424/285 |
| 4,478,849 | 10/1984 | Ainsworth et al. | 424/285 |
| 4,497,813 | 2/1985 | Ostermayer et al. | 514/166 |
| 4,503,067 | 3/1985 | Wiedemann et al. | 514/411 |
| 4,513,001 | 4/1985 | Joannic et al. | 514/394 |
| 4,636,511 | 1/1987 | Ostermayer et al. | 514/311 |
| 4,652,679 | 3/1987 | Alig et al. | 564/86 |
| 4,697,022 | 9/1987 | Leinert | 548/444 |
| 4,727,067 | 2/1988 | Ostermayer et al. | 514/162 |
| 4,751,246 | 6/1988 | Philion | 514/649 |
| 4,772,631 | 9/1988 | Holloway et al. | 514/539 |
| 4,892,886 | 1/1990 | Alig et al. | 514/567 |
| 4,940,800 | 7/1990 | Bertolini et al. | 548/327 |
| 4,960,783 | 10/1990 | Bonse et al. | 514/387 |
| 4,977,148 | 12/1990 | Holloway et al. | 514/183 |
| 5,013,761 | 5/1991 | Beedle et al. | 514/650 |
| 5,064,863 | 11/1991 | Alig et al. | 514/563 |

(List continued on next page.)

FOREIGN PATENT DOCUMENTS

| | | |
|---|---|---|
| 0 040 000 | 11/1981 | European Pat. Off. . |
| 0 052 963 | 6/1982 | European Pat. Off. . |
| 0 066 351 | 8/1982 | European Pat. Off. . |
| 0 061 907 | 10/1982 | European Pat. Off. . |
| 0 063 004 | 10/1982 | European Pat. Off. . |
| 0 068 669 | 1/1983 | European Pat. Off. . |
| 0 070 134 | 1/1983 | European Pat. Off. . |
| 0 082 665 | 6/1983 | European Pat. Off. . |
| 0 089 154 | 9/1983 | European Pat. Off. . |
| 0 091 749 | 10/1983 | European Pat. Off. . |
| 0 095 827 | 12/1983 | European Pat. Off. . |
| 0 099 707 | 2/1984 | European Pat. Off. . |
| 0 102 213 | 3/1984 | European Pat. Off. . |
| 0 171 702 | 2/1986 | European Pat. Off. . |
| 0 196 849 | 10/1986 | European Pat. Off. . |
| 0 211 721 | 2/1987 | European Pat. Off. . |
| 0 236 624 | 9/1987 | European Pat. Off. . |
| 0 328 251 A3 | 1/1989 | European Pat. Off. . |
| 0 386 920 | 9/1990 | European Pat. Off. . |
| 0 436 435 A1 | 7/1991 | European Pat. Off. . |
| 0 455 006 A2 | 11/1991 | European Pat. Off. . |
| 0 500 443 A1 | 8/1992 | European Pat. Off. . |
| 0 565 317 A1 | 10/1993 | European Pat. Off. . |
| 0 611 003 A1 | 2/1994 | European Pat. Off. . |
| 40 40 186 A1 | 6/1991 | Germany . |
| 636 856 A5 | 6/1983 | Switzerland . |
| 1 391 828 | 4/1975 | United Kingdom . |
| 1 532 380 | 11/1978 | United Kingdom . |
| 1 549 945 | 8/1979 | United Kingdom . |
| 1 571 231 | 7/1980 | United Kingdom . |
| 92/18461 | 10/1992 | WIPO . |
| 93/22277 | 11/1993 | WIPO . |
| 94/02493 | 2/1994 | WIPO . |
| 94/03425 | 2/1994 | WIPO . |
| 94/29290 | 12/1994 | WIPO . |
| 95/01170 | 1/1995 | WIPO . |
| 95/04047 | 2/1995 | WIPO . |

OTHER PUBLICATIONS

Tejani–Butt and Brunswick. "Synthesis an β–Adrenergic Receptor Blocking Potency of 1–(Substituted amino)–3–(4–indolyloxy)propan–2–ols" *J. Med. Chem.* 29:1524–1527 (1986).

Bürgisser, et al. "Alternative Explanation for the Apparent 'Two–Step' Binding Kinetics of High–Affinity Racemic Antagonist Radioligands" *Molecular Pharmacology* 19:509–512 (1981).

Marinetti, et al. "Beta–Adrenergic Receptors of Human Leukocytes" *Biochemical Pharmacology* 32(13):2033–2043 (1983).

Howe, et al. "Selective b3–adrenergic agonists of brown adipose tissue and thermogenesis" *J. Pharmacology* 117:69. Abstrct 40209r (1992).

*Primary Examiner*—José G. Dees
*Assistant Examiner*—Laura R. C. Lutz
*Attorney, Agent, or Firm*—Jeffrey J. Skelton; David E. Boone

[57] ABSTRACT

The present invention is in the field of medicine, particularly in the treatment of Type II diabetes and obesity. More specifically, the present invention relates to selective β3 adrenergic receptor agonists useful in the treatment of Type II diabetes and obesity. The invention provides compounds and method of treating type II diabetes, comprising administering to a mammal in need thereof compounds of the Formulas I and II:

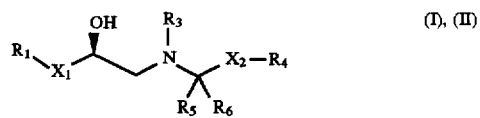

20 Claims, No Drawings

U.S. PATENT DOCUMENTS

| | | | |
|---|---|---|---|
| 5,166,218 | 11/1992 | Alig et al. | 514/652 |
| 5,254,595 | 10/1993 | Guzzi et al. | 514/652 |
| 5,321,036 | 6/1994 | Sher | 514/365 |
| 5,393,772 | 2/1995 | Yue et al. | 514/410 |
| 5,420,294 | 5/1995 | Beedle et al. | 548/507 |
| 5,453,436 | 9/1995 | Ohlstein | 514/411 |
| 5,534,640 | 7/1996 | Tegeler et al. | 549/80 |
| 5,541,197 | 7/1996 | Fisher et al. | 514/311 |
| 5,541,204 | 7/1996 | Sher et al. | 514/359 |
| 5,561,142 | 10/1996 | Fisher et al. | 514/312 |
| 5,574,164 | 11/1996 | Tegeler et al. | |

SELECTIVE β3 ADRENERGIC AGONISTS

This application is a division, of application Ser. No. 08/708,621 filed Sep. 5, 1996, now abandoned which is based on a provisional application 60/004,082 filed Sep. 21, 1995.

FIELD OF INVENTION

The present invention is in the field of medicine, particularly in the treatment of Type II diabetes and obesity. More specifically, the present invention relates to selective $\beta_3$ adrenergic receptor agonists useful in the treatment of Type II diabetes and obesity.

BACKGROUND OF THE INVENTION

The current preferred treatment for Type II, non-insulin dependent diabetes as well as obesity is diet and exercise, with a view toward weight reduction and improved insulin sensitivity. Patient compliance, however, is usually poor. The problem is compounded by the fact that there are currently no approved medications that adequately treat either Type II diabetes or obesity. The invention described herein is directed toward an effective and timely treatment for these serious diseases.

One therapeutic opportunity that has recently been recognized involves the relationship between adrenergic receptor stimulation and anti-hyperglycemic effects. Compounds that act as $\beta_3$ receptor agonists have been shown to exhibit a marked effect on lipolysis, thermogenesis and serum glucose levels in animal- models of Type II (non-insulin dependent) diabetes.

The $\beta_3$ receptor, which is found in several types of human tissue including human fat tissue, has roughly 50% homology to the $\beta_1$ and $\beta_2$ receptor subtypes yet is considerably less abundant. The importance of the $\beta_3$ receptor is a relatively recent discovery since the amino-acid sequence of the human receptor was only elucidated in the late 1980's. A large number of publications have appeared in recent years reporting success in discovery of agents that stimulate the $\beta_3$ receptor. Despite these recent developments, there remains a need to develop a selective $\beta_3$ receptor agonist which has minimal agonist activity against the $\beta_1$ and $\beta_2$ receptors. In addition, indolylpropanolamines have been disclosed by Beedle et. al. U.S. Pat. No. 5,013,761.

The present invention provides compounds which are selective $\beta_3$ receptor agonists. As such, the compounds effectively lead to an increase in insulin sensitivity and are useful in treating Type II diabetes and other ailments implicated by the $\beta_3$ receptor, without cardiac or tremor-related side effects.

SUMMARY OF INVENTION

The present invention encompasses novel compounds described by Formula I below.

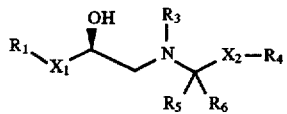

wherein:

$X_1$ is —OCH$_2$—, —SCH$_2$—, or a bond;

$R_1$ is a fused heterocycle of the formula:

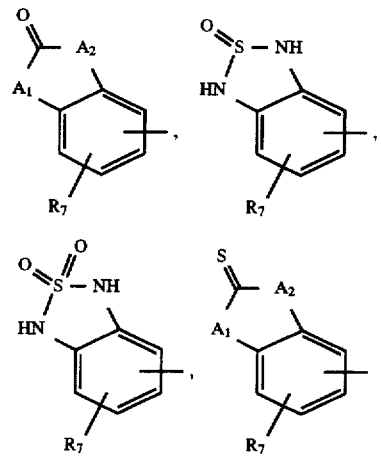

$R_2$ and $R_3$ are independently H, $C_1$–$C_4$ alkyl, or aryl;
$R_4$ is an optionally substituted heterocycle or a moiety selected from the group consisting of:

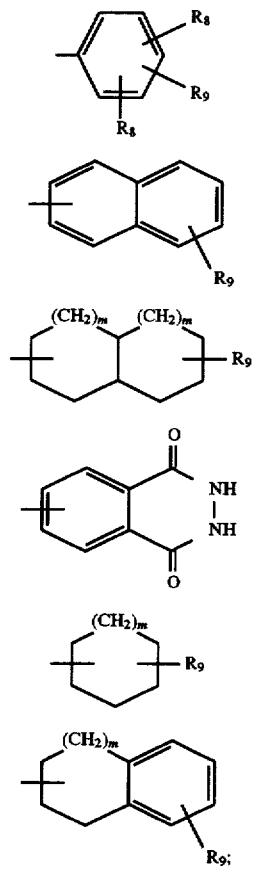

$X_2$ is a bond, or a 1 to 5 carbon straight or branched alkylene;
$R_5$ is H, or $C_1$–$C_4$ alkyl;
$R_6$ is H, or $C_1$–$C_4$ alkyl;
or $R_5$ and $R_6$ combine with the carbon to which each is attached to form a $C_3$–$C_6$ cycloalkyl;
or $R_6$ combines with to $X_2$ and the carbon to which $x_2$ is attached to form a $C_3$–$C_8$ cycloalkyl;

or $R_6$ combines with $X_2$, the carbon to which $X_2$ is attached, and $R_4$ to form:

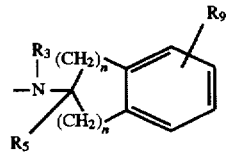

provided that $R_5$ is H;

$R_7$ is H, halo, hydroxy, $C_1$–$C_4$ alkyl, $C_1$–$C_4$ haloalkyl, aryl, CN, $COOR_2$, $CONHR_2$, $NHCOR_2$, $OR_2$, $NHR_2$, $SR_2$, $SO_2R_2$, $SO_2NHR_2$, or $SOR_2$;

$R_8$ is independently H, halo or $C_1$–$C_4$ alkyl;

$R_9$ is halo, CN, $OR_{10}$, $C_1$–$C_4$ alkyl, $C_1$–$C_4$ haloalkyl, $CO_2R_2$, $CONR_{11}R_{12}$, $CONH(C_1$–$C_4$ alkyl or $C_1$–$C_4$ alkoxy), $SR_2$, $CSNR_2$, $CSNR_{11}R_{12}$, $SO_2R_2$, $SO_2NR_{11}R_{12}$, $SOR_2$, $NR_{11}R_{12}$, optionally substituted aryl, optionally substituted heterocycle, or $C_2$–$C_4$ alkenyl substituted with CN, $CO_2R_2$ or $CONR_{11}R_{12}$;

$R_{10}$ is $C_1$–$C_4$ alkyl, $C_1$–$C_4$ haloalkyl, $(CH_2)nC_3$–$C_8$ cycloalkyl, $(CH_2)$naryl, $(CH_2)$nheterocycle, $(CH_2)nC_3$–$C_8$ optionally substituted cycloalkyl, $(CH_2)n$ optionally substituted aryl, $(CH_2)n$ optionally substituted heterocycle;

$R_{11}$ and $R_{12}$ are independently H, $C_1$–$C_4$ alkyl, aryl, $(CH_2)$naryl, or combine with the nitrogen to which each is bound to form morpholinyl, piperidinyl, pyrrolidinyl, or piperazinyl;

$A_1$ and $A_2$ are independently O, S, NH, $CH_2$, $NCH_3$, or $NCH_2CH_3$;

m is 0 or 1;

n is 0, 1, 2, or 3;

or a pharmaceutically acceptable salt thereof.

The present invention also encompasses novel compounds described by Formula II below.

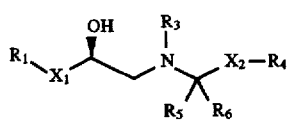

wherein:

$R_1$ is

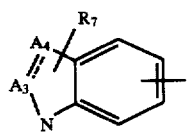

$X_1$ is —$OCH_2$—, —$SCH_2$—, or a bond;

The bond between $A_1$ and $A_4$ is either a single or double bond;

$A_3$ and $A_4$ are independently carbon or nitrogen;

$R_2$ and $R_3$ are independently H, $C_1$–$C_4$ alkyl, or aryl;

$R_4$ is an optionally substituted heterocycle or a moiety selected from the group consisting of:

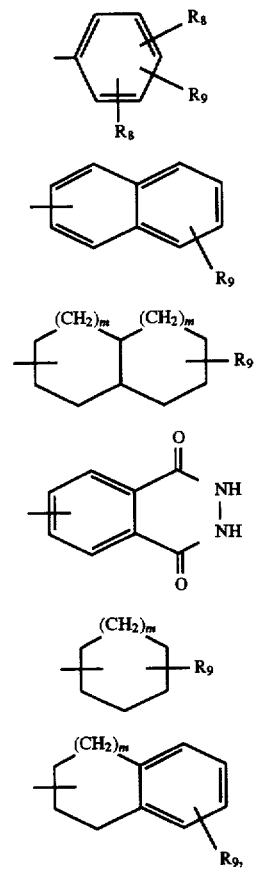

$X_2$ is a bond, or a 1 to 5 carbon straight or branched alkylene;

$R_5$ is H, or $C_1$–$C_4$ alkyl;

$R_6$ is H, or $C_1$–$C_4$ alkyl;

or $R_5$ and $R_6$ combine with the carbon to which each is attached to form a $C_3$–$C_6$ cycloalkyl;

or $R_6$ combines with to $X_2$ and the carbon to which $X_2$ is attached to form a $C_3$–$C_8$ cycloalkyl;

or $R_6$ combines with $X_2$, the carbon to which $X_2$ is attached, and $R_4$ to form:

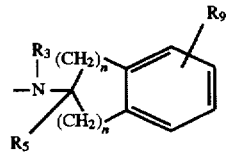

provided that $R_5$ is H;

$R_7$ is H, halo, hydroxy, $C_1$–$C_4$ alkyl, $C_1$–$C_4$ haloalkyl, aryl, CN, $COOR_2$, $CONHR_2$, $NHCOR_2$, $OR_2$, $NHR_2$, $SR_2$, $SO_2R_2$, $SO_2NHR_2$, or $SOR_2$;

$R_8$ is independently H, halo or $C_1$–$C_4$ alkyl;

$R_9$ is halo, CN, $OR_{10}$, $C_1$–$C_4$ alkyl, $C_1$–$C_4$ haloalkyl, $CO_2R_2$, $CONR_{11}R_{12}$, $CONH(C_1$–$C_4$ alkyl or $C_1$–$C_4$ alkoxy), $SR_2$, $CSNR_2$, $CSNR_{11}$ $R_{12}$, $SO_2R_2$, $SO_2NR_{11}R_{12}$, $SOR_2$, $NR_{11}R_{12}$, optionally substituted aryl, optionally substituted heterocycle, or $C_2$–$C_4$ alkenyl substituted with CN, $CO_2R_2$ or $CONR_{11}$ $R_{12}$;

$R_{10}$ is $C_1$–$C_4$ alkyl, $C_1$–$C_4$ haloalkyl, $(CH_2)nC_3$–$C_8$ cycloalkyl, $(CH_2)$naryl, $(CH_2)$nheterocycle, $(CH_2)nC_3$–$C_8$ optionally substituted cycloalkyl, $(CH_2)n$ optionally substituted aryl, or (CH$_2$)n optionally substituted heterocycle;

R$_{11}$ and R$_{12}$ are independently H, C$_1$–C$_4$ alkyl, aryl, (CH$_2$)naryl or combine with the nitrogen to which each is bound to form morpholinyl, piperidinyl, pyrrolidinyl, or piperazinyl;

m is 0 or 1;

n is 0, 1, 2,or 3; or a pharmaceutically acceptable salt thereof.

The present invention also provides for novel intermediates, useful in the preparation of compounds of Formulas I and II, described by Formula III below.

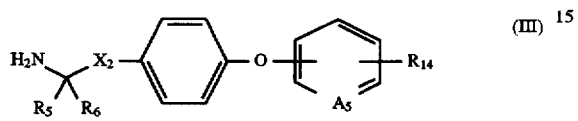
(III)

wherein:

A$_5$ is CH or N;

X$_2$ is a bond or a 1 to 5 carbon straight or branched alkylene.

R$_5$ is H, C$_1$–C$_4$ alkyl;

R$_6$ is H, C$_1$–C$_4$ alkyl;

or R$_5$ and R$_6$ combine with the carbon to which each is attached to form a C$_3$–C$_6$ cycloalkyl;

or R$_6$ combines with X$_2$ and the carbon to which X$_2$ is attached to form a C$_3$–C$_8$ cycloalkyl;

R$_{14}$ is C$_1$–C$_4$ alkyl, C$_1$–C$_4$ haloalkyl, hydroxy, carboxy, tetrazolyl, acyl, COOR$_2$, CONR$_{11}$R$_{12}$, CONH(C$_1$–C$_4$ alkoxy), cyano, C$_1$–C$_4$ alkoxy, C$_1$–C$_4$ alkyl, phenyl, nitro, NR$_{11}$R$_{12}$, NHCO(C$_1$–C$_4$ alkyl), NHCO(benzyl), NHCO(phenyl), SR$_2$, S(C$_1$–C$_4$ alkyl), OCO(C$_1$–C$_4$ alkyl), SO$_2$(NR$_{11}$R$_{12}$), SO$_2$(C$_1$–C$_4$ alkyl), or SO$_2$(phenyl);

or pharmaceutically acceptable salts thereof.

The present invention also provides novel processes for making, as well as novel pharmaceutical formulations of, compounds of Formulas I and II.

The compounds of the present invention are selective β$_3$ receptor agonists and as such are useful for treating Type II diabetes and obesity, as well as useful for agonizing the β$_3$ receptor. Therefore, the present invention also provides for methods of treating Type II diabetes and obesity, as well as a method of agonizing the β$_3$ receptor.

In addition, the present invention provides the use of compounds of Formulas I and II for treating Type II diabetes and obesity as well the use of compounds of Formulas I and II for agonizing the β$_3$ receptor.

Another representation of the compounds of the present invention is given by Formula IV below.

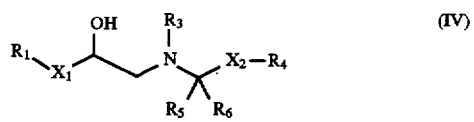
(IV)

wherein:

R$_1$ is a fused heterocycle of the formula:

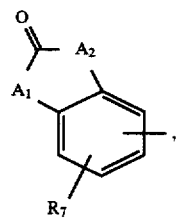
(a)

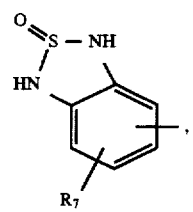
(b)

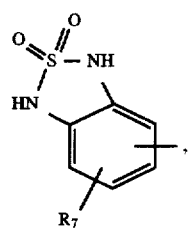
(c)

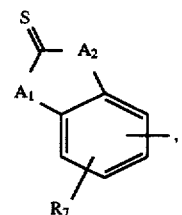
(d)

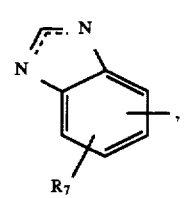
(e)

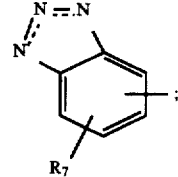
(f)

R$_2$ is H, C$_1$–C$_4$ alkyl, or aryl;

R$_3$ is H, C$_1$–C$_4$ alkyl, aryl, or heterocycle;

R$_4$ is an optionally substituted heterocycle or a moiety selected from the group consisting of:

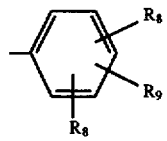
(g)

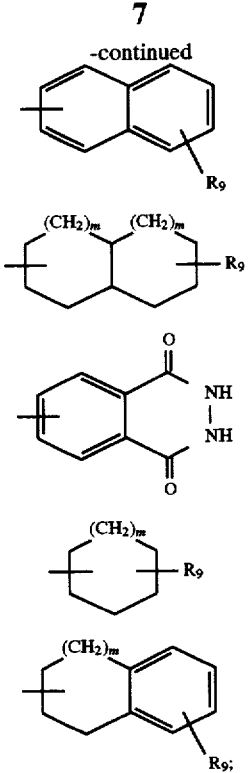

$R_5$ is H. or $C_1$–$C_4$ alkyl;

$R_6$ is H. $C_1$–$C_4$ alkyl, bonds to $X_2$ to form a $C_3$–$C_8$ cycloalkyl, or combines with $X_2$ and $R_4$ to form:

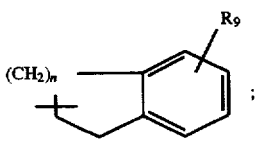

$R_7$ is H, halo, hydroxy, $C_1$–$C_4$ alkyl, $C_1$–$C_4$ alkoxy, $NH_2$, $SR_2$, $SO_2R_2$, or $SOR_2$;

$R_8$ is independently H, halo or $C_1$–$C_4$ alkyl;

$R_9$ is halo, CN, $OR_{10}$, $C_1$–$C_4$ alkyl, $C_1$–$C_4$ haloalkyl, $CO_2R_2$, $CONR_{11}R_{12}$, $CONH(C_1$–$C_4$ alkyl or $C_1$–$C_4$ alkoxy), $SR_2$, $CSNR_2$, $CSNR_{11}R_{12}$, $SO_2R_2$, $SO_2NR_{11}R_{12}$, $SOR_2$, $NR_{11}R_{12}$, optionally substituted aryl, optionally substituted aryloxy, optionally substituted heterocycle, or $C_2$–$C_4$ alkenyl optionally substituted with CN, $CO_2R_2$ or $CONR_{11}R_{12}$;

$R_{10}$ is independently $C_1$–$C_4$ alkyl, $C_1$–$C_4$ haloalkyl, $(CH_2)nC_3$–$C_8$ cycloalkyl, $(CH_2)$naryl, $(CH_2)$nheterocycle, said aryl, $C_3$–$C_8$ cycloalkyl, or heterocycle being optionally substituted;

$R_{11}$ and $R_{12}$ are independently H, $C_1$–$C_4$ alkyl, or combine with the nitrogen to which each are bound to form a morpholinyl, piperdinyl, pyrrolyl, or piperazine;

$A_1$ and $A_2$ are independently O, S, NH, or $NCH_3$;

$X_1$ is —$OCH_2$—, —$SCH_2$—, or absent;

$X_2$ is absent or a 1 to 5 carbon straight or branched alkylene;

m is 0 or 1;

n is 0, 1, 2, or 3;

or a pharmaceutically acceptable salt or solvate thereof.

DETAILED DESCRIPTION

For the purposes of the present invention, as disclosed and claimed herein, the following terms are defined below. As they relate to the present invention, the terms below may not be interpreted, individually or collectively, to describe chemical structures that are unstable or impossible to construct.

The term "halo" represents fluorine, chlorine, bromine, or iodine.

The term "$C_1$–$C_4$ alkyl" represents a cyclo, straight or branched chain alkyl group having from one to four carbon atoms such as methyl, ethyl, n-propyl, isopropyl, cyclopropyl, n-butyl, isobutyl, sec-butyl, t-butyl and the like. A "haloalkyl" is one such alkyl substituted with one or more halo atoms, preferably one to three halo atoms. An example of a haloalkyl is trifluoromethyl. An "alkoxy" is a alkyl group covalently bonded by an —O— linkage.

The term "1 to 5 carbon straight or branched alkylene" represents a one to five carbon, straight or branched, alkylene moiety. A branched alkylene may have one or more points of branching. A 1 to 5 carbon straight or branched alkylene may optionally be unsaturated at one or more carbons. Thus, a 1 to 5 carbon straight or branched alkylene includes 1 to 5 carbon alkylene, alkenylene and alkylidene moieties. Examples include methylene, ethylene, propylene, butylene, —$CH(CH_3)CH_2$— $CH(C_2H_5)CH_2$—, —$CH(CH_3)CH(CH_3)$—, —$CH_2C(CH_3)_2$—, —$CH_2CH(CH_3)CH_2$—, —$C(CH_3)_2CH$=, —CH=$CHCH_2$—, —CH=CH—, and the like.

The "acyl" moiety, alone or in combination, is derived from an alkanoic acid containing from one to seven carbon atoms. The term "acyl" also includes moieties derived from an aryl carboxylic acid.

The term "aryl" represents an optionally substituted or unsubstituted phenyl or naphthyl. The term ($CH_2$)naryl is preferably benzyl or phenyl.

The notation "- - -" when used in conjunction with a bond indicates that bond may either be a double bond or a single bond.

The term "optionally substituted" as used herein means an optional substitution of one to three, preferably one or two groups independently selected from halo, $C_1$–$C_4$ haloalkyl, hydroxy, carboxy, tetrazolyl, acyl, $COOR_2$, $CONR_{11}R_{12}$, $CONH(C_1$–$C_4$ alkoxy), cyano, $C_1$–$C_4$ alkoxy, $C_1$–$C_4$ alkyl, phenyl, benzyl, nitro, $NR_{11}R_{12}$, $NHCO(C_1$–$C_4$ alkyl), NHCO(benzyl), NHCO(phenyl), $SR_2$,$S(C_1$–$C_4$ alkyl), OCO ($C_1$–$C_4$ alkyl), $SO_2(NR_{11}R_{12})$, $SO_2(C_1$–$C_4$ alkyl), or $SO_2$ (phenyl); provided that such substitution does not entirely destroy biological activity, as defined in this specification.

$R_{11}$ and $R_{12}$ are independently H, $C_1$–$C_4$ alkyl, or combine with the nitrogen to which each is bound to form morpholinyl, piperidinyl, pyrrolidinyl, or piperazinyl.

The term "heterocycle" represents a stable, optionally substituted or unsubstituted, saturated or unsaturated 5 or 6 membered ring, said ring having from one to four heteroatoms that are the same or different and that are selected from the group consisting of sulfur, oxygen, and nitrogen; and when heterocycle contains two adjacent carbon atoms, the adjacent carbon atoms may be structured to form a group of the formula —CH=CH—; provided that (1) when the heterocyclic ring contains 5 members, the heteroatoms comprise not more than two sulfur or two oxygen atoms but not both; and (2) when the heterocyclic ring contains 6 members and is aromatic, sulfur and oxygen are not present. The heterocycle may be attached at any carbon or nitrogen which affords a stable structure. The heterocycle may be optionally substituted. Examples of an heterocycle include pyrazole, pyrazoline, imidazole, isoxazole, triazole, tetrazole, oxazole, 1,3-dioxolone, thiazole, oxadiazole, thiadiazole, pyridine, pyrimidine, piperazine, morpholine, pyrazine, pyrrolidine, piperidine, oxazolidone, oxazolidinedione, imidazolidinone.

The term "leaving group" as used in the specification is understood by those skilled in the art. Generally, a leaving group is any group or atom that enhances the electrophilicity of the atom to which it is attached for displacement. Preferred leaving groups are p-nitrobenzene sulfonate, triflate, mesylate, tosylate, imidate, chloride, bromide, and iodide.

The term "pharmaceutically effective amount", as used herein, represents an amount of a compound of the invention that is capable of agonizing the $\beta_3$ receptor in mammals. The particular dose of the compound administered according to this invention will, of course, be determined by the particular circumstances surrounding the patient, including the compound administered, the route of administration, the particular condition being treated, and similar considerations.

The term unit "dosage form" refers to physically discrete units suitable as unitary dosages for human subjects and other mammals, each unit containing a predetermined quantity of active material calculated to produce the desired therapeutic effect, in association with a suitable pharmaceutical carrier.

The term "treating," as used herein, describes the management and care of a patient for the purpose of combating the disease, condition, or disorder and includes the administration of a compound of present invention to prevent the onset of the symptoms or complications, to alleviate symptoms or complications, or to eliminate the disease, condition, or disorder.

The term "agonizing," as used herein, means stimulating or affecting a receptor to elicit a pharmacological response.

The term "selective" means preferential agonism of the $\beta_3$ receptor over agonism of the $\beta_1$ or $\beta_2$ receptor. In general, the compounds of the present invention demonstrate at a minimum a twenty fold differential (preferably over a 50× differential) in the dosage required to behave as an agonist to the $\beta_3$ receptor and the dosage required for equal agonism of the $\beta_1$ and $\beta_2$ as measured in the Functional Agonist Assay. The compounds demonstrate this differential across the range of doses. Thus, $\beta_3$ selective compounds behave as agonists for the $\beta_3$ receptor at much lower concentrations with lower toxicity by virtue of their minimal agonism of the other receptors.

As previously noted, the present invention provides a method of treating type II diabetes and obesity, comprising administering to a mammal in need thereof compounds of the Formulas I and II. Preferred embodiments of the present invention are set out in paragraphs below.

Preferred compounds are those of Formulas I and II, wherein:

(a) $R_1$ is

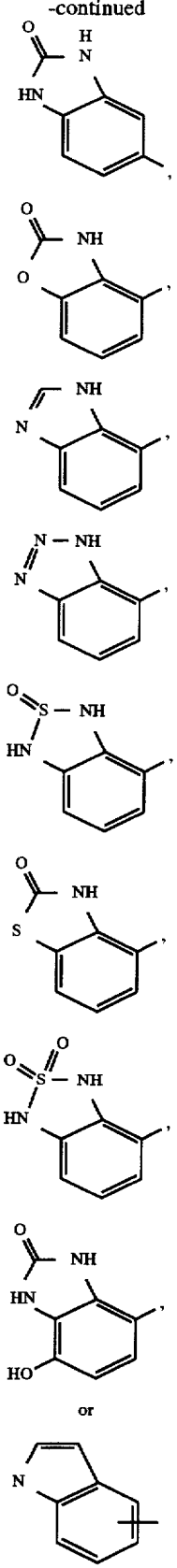

(b) $X_1$ is —OHC$_2$—, the oxygen of which is attached to $R_1$.

(c) $X_1$ is a bond.
(d) $R_5$ and $R_6$ are independently $C_1$–$C_4$ alkyl.
(e) $X_2$ is isopropylene, ethylene, methylene, or a bond.
(f) $R_4$ is

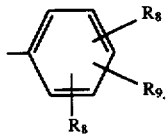

(g) $R_4$ is

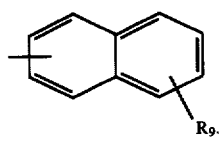

Other preferred compounds are those of Formulas I and II, wherein:

(aa) $R_1$ is

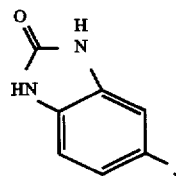

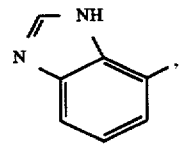

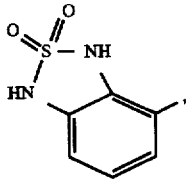

or (bb) $R_5$ and $R_6$ are methyl or ethyl.
(cc) $X_2$ is methylene or ethylene.
(dd) $R_8$ is hydrogen.
(ee) $R_8$ is halo.
(ff) $R_9$ is $OR_{10}$.

(gg) $R_9$ is $CONR_{11}R_{12}$.
(hh) $R_9$ is CN.
(ii) $R_9$ is optionally substituted aryl.
(jj) $R_{10}$ is $(CH_2)$naryl, $(CH_2)$nheterocycle, $(CH_2)$n optionally substituted aryl, or $(CH_2)$n optionally substituted heterocycle.

More preferred compounds are those of Formula Ia, Ib, Ic, and Id:

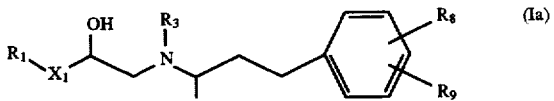 (Ia)

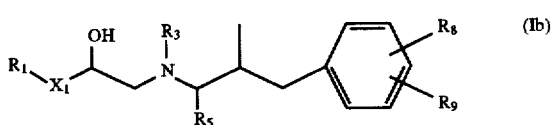 (Ib)

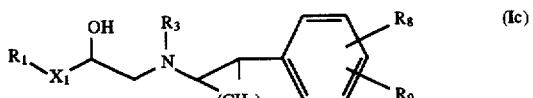 (Ic)

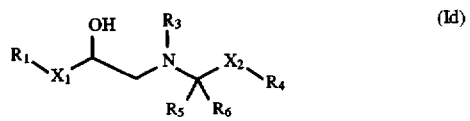 (Id)

Especially preferred compounds are those of Formulas Ia, Ib, Ic, or Id wherein: $R_1$ is

or

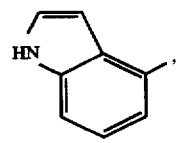

$X_1$ is —$OHC_2$—the oxygen of which is attached to $R_1$, $R_3$ is H, and $R_9$ is $CONH_2$ or $OR_{10}$, wherein $R_{10}$ is a optionally substituted aryl, particularly phenyl, or optionally substituted heterocycle, particularly pyridine.

Other especially preferred compounds include the following:

(S, R and S, S) 4-(3-[N-(2-[4-(5-carbamoyl-2-pyridyloxy)phenyl]-1-methylethyl)amino]-2-hydroxypropoxy)-1,3-dihydro-2H-benzimidazol-2-one (S, R and S, S) 5-(3-[N-(3-[2-oxo-1,3-dihydro-2H-benzimidazole-4-yloxy]-2-hydroxypropyl)amino]butyl)-2-thiophenesulfonamide (S, R and S, S) 4-(3-[N-(3-[4-(4-carbamoylphenoxy)phenyl]-1-methylpropyl)amino]-2-hydroxypropoxy)-1,3-dihydro-2H-benzimidazol-2-one (All isomers of:) 5-(4-[3-(N-[3-(2-oxo-1,3-dihydro-2H-benzimidazole-4-yloxy)-2-hydroxypropyl]amino)-2-methylbutyl]-3-fluorophenyl)-1H-tetrazole (All isomers of:) 4-(3-[N-(2-[(4-carbamoylphenyl)methyl]-1-methylpropyl)amino]-2-hydroxypropoxy)-1,3-dihydro-2H-benzimidazol-2-one Most preferred comounds include the following structures:

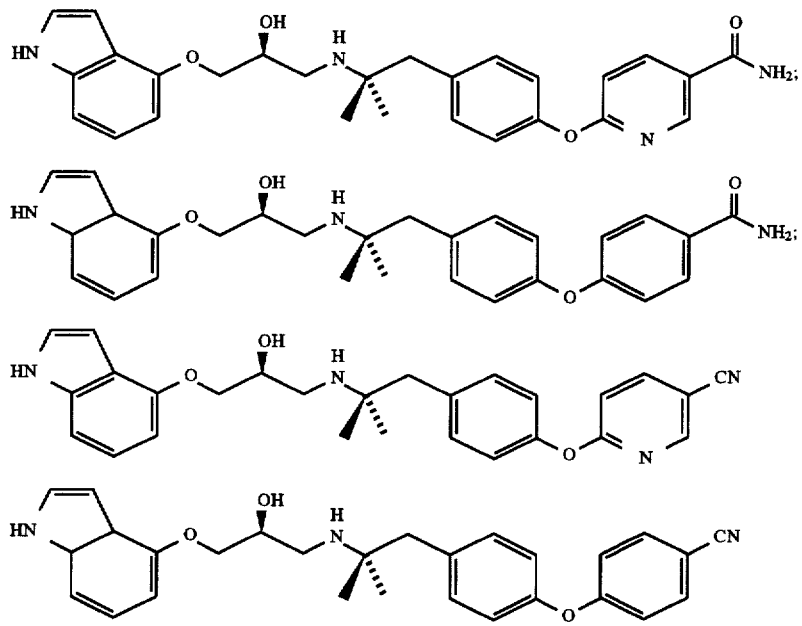

By virtue of their acidic moieties, the compounds of Formulas I and II include the pharmaceutical acceptable base addition salts thereof. Such salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

Because of the basic moiety, the compounds of Formulas I and II can also exist as pharmaceutically acceptable acid addition salts. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4 dioate, 3-hexyne-2, 5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycollate, maleate, tartrate, methanesulfonate, propanesulfonate, naphthalene-1-sulfonate, naphthalene-2-sulfonate, mandelate and the like salts.

It is recognized that various stereoisomic forms of the compounds of Formulas I and II may exist. The compounds may be prepared as racemates and can be conveniently used as such. Therefore, the racemates, individual enantiomers, diastereomers, or mixtures thereof form part of the present invention. Unless otherwise specified, whenever a compound is described or referenced in this specification all the racemates, individual enantiomers, diastereomers, or mixtures thereof are included in said reference or description.

It is also recognized that various tautomeric forms of the compounds of Formulas I and II may exist, and all tautomeric forms are part of the present invention. Unless otherwise specified, whenever a compound is described or referenced in this specification all tautomeric forms, or mixtures thereof, are included in said reference or description.

The compounds of Formulas I and II are prepared as described in the following Schemes and Examples. Schemes 1 and 2 describe methodology for the preparation of final embodiments of the present invention. Schemes 3–5 describe methodology for the preparation of intermediates required for the construction of the final embodiments of the invention.

Scheme I

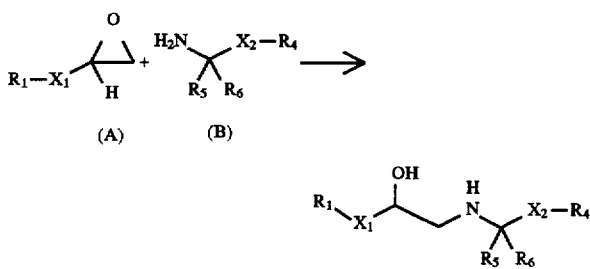

In Scheme I, $X_1$, $X_2$, $R_1$, $R_2$, $R_4$, $R_5$, and $R_6$ have the same meaning as previously described. The reaction of Scheme I is carried out under conditions appreciated in the art for the amination of epoxides. For example, the epoxide (A) may be combined with the amine (B) in an alcohol, preferably, ethanol at room temperature to the reflux temperature of the reaction mixture. Preferably, the reaction is carried under conditions generally described in Atkins et al., *Tetrahedron Lett.* 27:2451 (1986). These conditions include mixing the reagents in the presence of trimethylsilyl acetamide in a polar aprotic solvent such as acetonitrile, dimethylformamide (DMF), acetone, dimethylsulfoxide (DMSO), dioxane, diethylene glycol dimethyl ether (diglyme), tetrahydrofuran (THF), or other polar aprotic solvents in which the reagents are soluble. Preferably, the solvent is DMSO. The reaction is carried out at temperatures ranging from about 0° C. to reflux.

Some of the compounds of the present invention are prepared by a novel combinatorial/parallel synthesis. This synthesis is described in Scheme II.

Scheme I

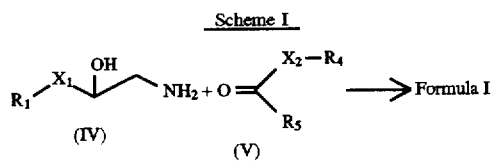

In Scheme II, $X_1$, $X_2$, $R_1$, $R_2$, $R_4$, and $R_5$ have the same meaning as previously described. $R_6$ is H. The reaction of Scheme II is preferably carried out by adding to a glass vial: a non-reactive solvent such as methanol, DMF, methylene chloride or acetonitrile, amine (IV), and ketone (V). The solution is shaken to allow for imine formation and treated with Amberlite IRA400 borohydride resin (Aldrich). The slurry is then shaken an additional 24 hours to effect reduction to the secondary amine. Methylene chloride and polystyrene-linked benzaldehyde resin (Frechet, J. M. et al., *J. Am Chem. Soc.* 93:492 (1971)) is added to the vial, in order to scavenge excess primary amine starting material. The slurry is shaken, preferably overnight. The slurry is then filtered through a cotton plug, and the residual solids rinsed with methanol. Evaporation under a flow of air, followed by drying for several hours at room temperature in a vacuum oven yields the desired product of sufficient purity A modification of Scheme II is necessary when the amine hydrochloride salt is used. Addition of resin-bound base to the initial reaction mixture prior to reduction or scavenging allows the desired reaction to proceed. Imine formation using amine hydrochloride salts, an aldehyde or ketone, and a resin bound amine base may be carried out using two different resins: poly(4-vinylpyridine), commercially available from Aldrich, and resin (VIII), synthesized by the reaction of Merrifield resin with piperidine (Scheme IIa):

Scheme IIa

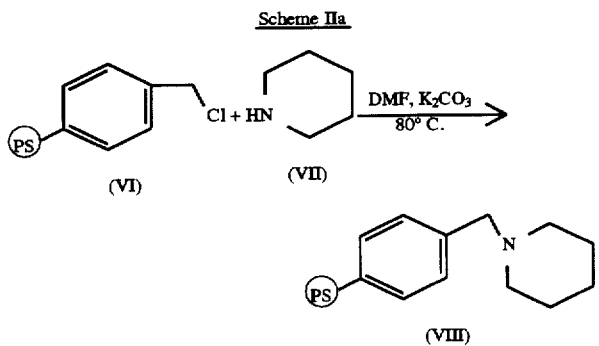

In Scheme IIa, PS is polysytrene. Both the poly(4-vinylpyridine) and resin (VIII) promote imine formation.

Scheme II can also be carried out by utilization of traditional fashion. Reductive aminations described in scheme II are well known in the art. They are typically performed by mixing the amine and ketone starting materials in a solvent and adding a reducing agent. Solvents typically include lower alcohols, DMF, and the like. A wide variety of reducing agents can be utilized, most commonly utilized are sodium borohydride and sodium cyanoborohydride. The reaction is typically performed at room temperature to the reflux temperature of the solvent. Products are isolated by techniques well known in the art.

The ketone and amino starting materials of Scheme II can be prepared by techniques recognized and appreciated by one skilled in the art. The synthesis of the starting materials is generally described in Schemes III and IV.

Scheme III

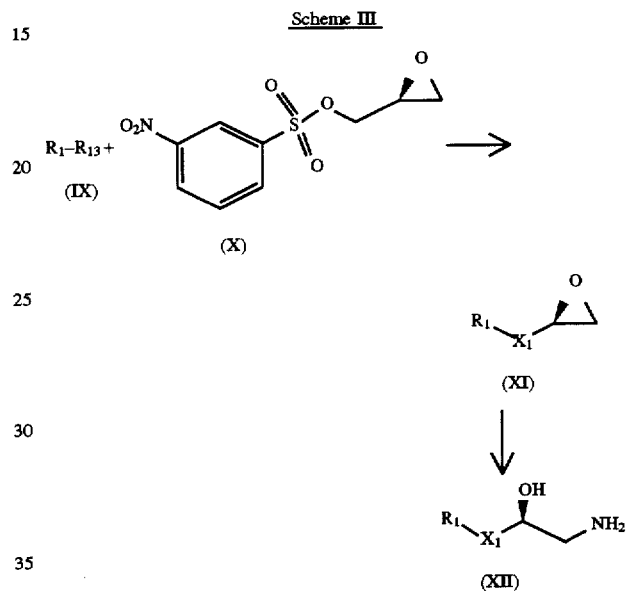

In Scheme III, $R_1$ is the same as previously defined. $R_{13}$ is OH or SH. Equimolar amounts of the aromatic compound (Compound IX) and (2S)-(+)-glycidyl 3-nitrobenzenesulfonate (Compound X) are dissolved in an inert solvent such as acetone and treated with 1.1 equivalents of a non-reactive acid scavenger, such as $K_2CO_3$. The suspension is then heated at reflux for 16-20 hours with stirring. The solvent is removed in vacuo. The residue is partitioned between chloroform or other organic solvent and water. The organic layer is dried over $Na_2SO4$ and concentrated in vacuo to give the epoxide (XI) in sufficient purity (>95%) and yield (85-100%).

The epoxide (XI) is dissolved in an alcohol, preferably methanol, and treated with one equivalent of dibenzylamine. The solution is preferably stirred at reflux for three to four hours and then cooled to ambient temperature. Approximately 10 equivalents of ammonium formate are added to the flask, followed by 10% palladium on carbon, and the suspension stirred vigorously at reflux for 30–45 minutes. The reaction mixture is then filtered through Celite, concentrated in vacuo to a minimum volume and treated with 1.1 equivalents of a 1.0 M anhydrous solution of HCl in ether. The solution is concentrated to dryness. The solid residue is triturated with pentane to yield products of sufficient purity (>97%) and yield (60–100%). If desired, further purification may be carried out by passing over a short plug of silica, eluting with $CHCl_3$, then 95:5 $CHCl_3$/MeOH, the 25:5:1 $CHCl_3$/ MeOH/$NH_4OH$.

Alternatively, the epoxide (XI) is treated with a solution of methanol saturated with ammonia gas and stirred at room temperature in a sealed tube for 16 hours. This solution is then evaporated, and the residue subjected to standard purifications such as column chromatography or recrystallization. The HCl salt is then optionally produced by the addition of HCl gas in ether.

The reaction of Scheme III is further described in Beedle et al., U.S. Pat. No. 5,013,761 and reference cited therein. U.S. Pat. No. 5,013,761 is herein incorporated by reference.

The ketone moieties of Scheme II, that are either unknown in the art or not commercially available, are prepared in accordance with Scheme IV.

Scheme IV

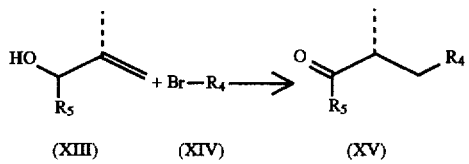

(XIII)  (XIV)  (XV)

In Scheme IV, $R_4$ and $R_5$ are the same as previously defined. The notation - - - indicates optional branching. Preferably, $R_4$ is a substituted phenyl. The reaction described in Scheme IV is referred to as a Heck reaction and is described in A. J. Chalk et al., *J. Org. Chem.* 41: 1206 (1976). The reaction is achieved by treating compound (XIII) with an arylpalladium reagent. The arylpalladium reagent is generated L situ by treating Compound (XIV) with a palladium-triarylphosphine complex. The reaction is generally carried out in under conditions appreciated in the art.

Additional amines, of the type where $X_2$ is methylene, $R_4$ is aryl, and $R_{10}$ is aryl, heterocycle, optionally substituted aryl, or optionally substituted heterocycle, that are reacted in a manner analogous to Scheme I are prepared in accordance with Scheme V.

affected at between 20 and 60 psi of hydrogen, and with a variety of solvents, temperatures, and catalysts well known in the art. The reaction is preferably carried out at 50 psi of hydrogen over 5% palladium on carbon wetted with 2B3 ethanol. Compound (XVII) is charged to the reactor along with one equivalent of acetic acid, diluted with methanol, heated to 50 degrees ° C., and subjected to hydrogen for 5–24 hours depending on the scale of the reaction. The product is isolated as the acetic acid salt upon work up by methods well known in the art.

A skilled artisan would appreciate that compounds of the formula (XVIII) could be coupled with a wide variety of aromatic halides to yield the claimed ethers. The coupling can be carried out according to procedures well known in the art and is preferably performed by mixing the starting materials in N, N-dimethylacetamide and toluene in the presence of potassium carbonate. The reaction is then heated to reflux for 5 to 24 hours and water removed. The product is typically isolated by aqueous work up after rotory evaporation of the reaction solvent. The crude product can be purified by methods well know in the art. A skilled artisan would appreciate that the amines prepared by Scheme V can be utilized in Scheme I to prepare compounds of the present invention. Scheme V also describes preparation of novel intermediates of the Formula III.

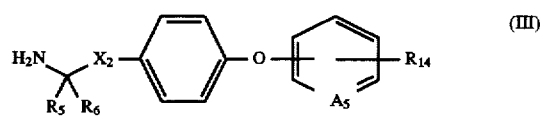

(III)

wherein:

$A_5$ is CH or N;

$X_2$ is a bond or a 1 to 5 carbon straight or branched alkylene.

$R_5$ is H, $C_1$–$C_4$ alkyl;

$R_6$ is H, $C_1$–$C_4$ alkyl;

Scheme V

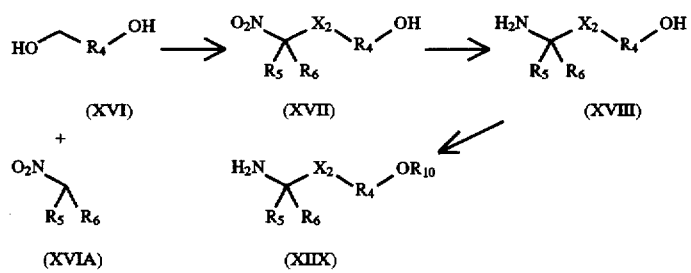

(XVI)  (XVII)  (XVIII)

(XVIA)  (XIIX)

Compounds of formula (XVII) can be prepared by reacting arylalkyl alcohols of formula (XVI) with excess (5 mol/equiv) of a compound of formula (XVIA) by methods well known in the art. (see Sh. Prikl. Kin., Vol 45, 1573–77 (1972); Russ). The reaction can also be carried out by mixing the reagents in an aprotic solvent, preferably diglyme, and adding potassium t-butoxide (0.5 mol/equiv.). The reaction is then heated to reflux and water removed. After removal of water is complete, generally 2–8 hours depending upon the scale of the reaction, the resulting solution is subjected to aqueous workup including acidic washes and the product is isolated by crystallization. Compounds of formula (XVIII) can be prepared by hydrogenation of the corresponding compounds of formula (XVII) over a precious metal catalyst. The hydrogenation can be or $R_5$ and $R_6$ combine with the carbon to which each is attached to form a $C_3$–$C_6$ cycloalkyl;

or $R_6$ combines with $X_2$ and the carbon to which $X_2$ is attached to form a $C_3$–$C_8$ cycloalkyl;

$R_{14}$ is $C_1$–$C_4$ alkyl, $C_1$–$C_4$ haloalkyl, hydroxy, carboxy, tetrazolyl, acyl, $COOR_2$, $CONR1R_{12}$, $CONH(C_1$–$C_4$ alkoxy), cyano, $C_1$–$C_4$ alkoxy, $C_1$–$C_4$ alkyl, phenyl, nitro, $NR_{11}R_{12}$, $NHCO(C_1$–$C_4$ alkyl), NHCO(benzyl), NHCO(phenyl), $SR_2$, $S(C_1$–$C_4$ alkyl), $OCO(C_1$–$C_4$ alkyl), $SO_2(NR_{11}R_{12})$, $SO_2(C_1$–$C_4$ alkyl), or $SO_2$(phenyl);

or pharmaceutically acceptable salts thereof.

Compounds of Formula III are useful in the preparation of compounds of Formulas I and II, and as such represent an additional embodiment of the present invention.

Another embodiment of the present invention is a process of preparing novel compounds of the formula IA

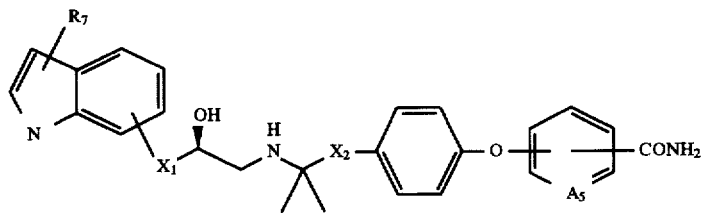

(IA)

wherein:
A₅ is CH or N;
which comprises:

in step 1, hydrolysis of a compound of the formula IB:

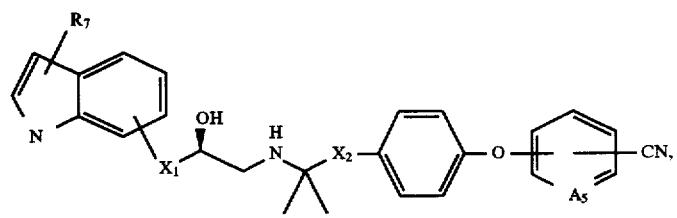

(IB)

and in step 2, reacting the product of step 1 to form an acid addition salt.

Step one of the process can be carried out by a variety of agents known in the art, it is however preferably affected by utilization of one of the following agents: polyphosphoric acid, $H_2O_2$ and $K_2CO_3$ in dimethylsulfoxide, $H_2O_2$ and ammonium hydroxide, $H_2O_2$ and sodium hydroxide, potassium hydroxide and t-butanol, or water and HCl. Step 2 of the process involves the addition of an agent capable of forming an acid addition salt with the product of step 1. Step 2 can be carried out by numerous methods known in the art involving the addition of a mineral acid, or other acid, to a solution of the product of step 1.

Another embodiment of the present invention is a process of preparing a compound of Formulas I and II which comprises:

In step 1,reacting an epoxide of the formula (XI):

(XI)

with an amine of formula:

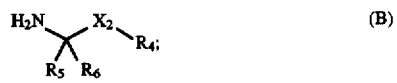

(B)

and in step 2, reacting the product of step 1 to form an acid addition salt.

The process can be carried out by a variety of agents known in the art, it is however preferably affected by reacting the amine and epoxide in a solvent at elevated temperature. Preferred solvents include: lower alcohols, dimethylformamide, dimethylsulfoxide, acetone and the like. The reaction is generally performed at a temperature ranging from ambient to the reflux temperature of the solvent. Most preferably, it is done in ethanol at 40°–60° C. Step 2 can be carried out by numerous methods known in the art involving the addition of a mineral acid, or other acid, to a solution of the product of step 1.

Starting materials for the compounds described in Schemes I, II, III, IV or V are either commercially available, known in the art, or can be prepared by methods known in the art or described herein.

PREPARATIONS AND Examples

The following examples and preparations are provided merely to further illustrate the invention. The scope of the invention is not construed as merely consisting of the following examples. In the following examples and preparations, melting point, nuclear magnetic resonance spectra, mass spectra, high pressure liquid chromatography over silica gel, gas chromatography, N,N-dimethylformamide, palladium on charcoal, tetrahydrofuran, ethyl acetate, thin layer chromatography and elemental analysis are abbreviated M.Pt., NMR, MS, HPLC, GC, DMF, Pd/C, THF, EtOAc, TLC and EA respectively. The terms "EA", "TLC", "NMR", and "MS", when being utilized in the preparations, indicate that the data indicated was consistent with the desired structure.

Preparations 1 through 18 encompass the methodology required to prepare the heterocyclic ethanol amines used in Scheme II to prepare final embodiments of the invention.

Preparation 1

(S)-3-(2-Amino-3-nitrophenoxy)-1,2-epoxypropane

A solution of 2-amino-3-nitrophenol (5.95 g, 38.6 mmol) and (2S)-(+)-glycidyl 3-nitrobenzenesulfonate (10.0 g, 38.6 mmol) in 150 mL of acetone was treated with 1.1 equivalents of $K_2CO_3$ (5.86 g, 42.4 mmol) and stirred at reflux for 18 hours. The suspension was cooled to ambient temperature; the solids were filtered; and the filtrate concentrated in vacuo to dryness. The resulting solids were partitioned between chloroform and water, and the aqueous layer extracted once with chloroform. The organic layers were combined and dried over $Na_2SO_4$ and concentrated in vacuo to 8.0 g (99%) of an orange solid. TLC (Rf =0.5, $CHCl_{13}$) and NMR indicated >95% purity, so the material was used without further purification. NMR.

Preparation 2

(S)-[3-(N,N-Dibenzylamino)-2-hydroxypropoxy]-2-amino-3-nitrobenzene (S)-3-(2-Amino-3-nitrophenoxy)-1,2-epoxypropane (8.0 g, 38.1 mmol) was dissolved in 250 mL of methanol and treated with dibenzylamine (8.05 mL, 42.0 mmol, d=1.026). The mixture was stirred at reflux for 10 hours and then cooled to 0° C. The resulting orange precipitate was filtered and washed with cold methanol, then dried to yield 12.1 g (78%) of a pale orange solid that was pure by NMR and TLC analysis. The material was used without further purification. NMR.

Preparation 3

(S) - [3 - (N, N-Dibenzylamino)-2-hydroxypropoxy]-2,3-diamino benzene (S)-[3-(N,N-Dibenzylamino)-2-hydroxypropoxy]-2-amino-3-nitrobenzene (10.6 g, 26.0 mmol) was suspended in 1 L of 2:1 ethanol/water at ambient temperature and treated with excesses of sodium bicarbonate (26.22 g, 0.31 mol) and sodium hydrosulfite (54.34 g, 0.31 mol). The orange reaction mixture slowly became colorless over 1 hour, and the mixture was left to stir at ambient temperature for 16 hours. The suspension was filtered, and the filtrate concentrated in vacuo to a leave a white solid. This residue was partitioned between chloroform and water, and the organic layer washed twice with brine. The combined organic extracts were concentrated in vacuo to give 8.8 g of a brown oil. The compound was recrystallized rapidly from toluene to give 7.96 g (81%) of pale brown needles. NMR.

Preparation 4

(S)-4-[2-Hydroxy-3-(N,N-dibenzylamino)propoxy]-1,3-dihydro-2H-benzimidazol-2-one (S)-[3-(N,N-Dibenzylamino)-2-hydroxypropoxy]-2,3-diaminobenzene (4.4 g, 11.6 mmol) was suspended in a mixture of toluene (60 mL) and 2N HCl (100 mL) at ambient temperature with vigorous stirring. An excess of triphosgene (17.3 g, 58.3 mmol) was added, and the stirring continued for 14 hours. The biphasic mixture was cautiously quenched and neutralized with sodium bicarbonate, causing an off-white precipitate to form at the interface. The precipitate was filtered and dried in vacuo to yield 4.35 g (93%) of a pale solid that was used without further purification. TLC, NMR and MS all indicated high purity of the intermediate.

Preparation 5

(S)-4-[2-Hydroxy-3-aminopropoxy]-1,3-dihydro-2H-benzimidazol-2-one

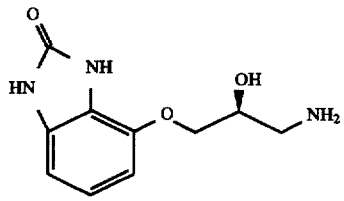

(S) 4-[2-Hydroxy-3-(N,N dibenzylamino) propoxy]-1,3-dihydro-2H-benzimidazol-2-one (4.35 g, 10.8 mmol) was dissolved in methanol (200 mL) and treated with a vast excess of ammonium formate (13.0 g, 0.21 mol), followed by 10% palladium on carbon (1.5 g). The suspension was stirred at reflux for 3 hours. After cooling the suspension, the reaction mixture was filtered through Celite. The filtrate concentrated in vacuo to a pale brown oil which slowly crystallized upon standing. The resulting solid was triturated using chloroform containing methanol and filtered to give 1.56 g (65%) as the desired product of a pale grey solid. NMR. MS.

Preparation 6

(S)-4-[2-(Dimethyl-tert-butylsilyl)oxy-3-(dibenzylamino) propoxy]benzimidazole (S)-[3-(N,N-Dibenzylamino)-2-hydroxypropoxy]-2,3-diaminobenzene (1g, 2.7mmol) was dissolved in N,N Dimethylformamide (10 mL) and imidazole (0.27g, 4.0 mmol) and tert-butyldimethylsilyl chloride (0.6g, 4.0 mmol) were added. The solution was stirred at ambient temperature for 18 hours and then was partitioned between chloroform and water. The combined organic extracts were dried over sodium sulfate and concentrated in vacuo to give the desired benzimidazole 1.3g (96%). NMR.

Preparation 7

(S)-4-[2-(Dimethyl-tert-butylsilyl)oxy-3-aminopropoxy)-benzimidazole

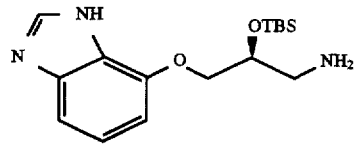

(S)-4-[2-(Dimethyl-tert-butylsilyl)oxy-3-(dibenzylamino)propoxy]benzimidazole (1.27g, 2.5mmol) was dissolved in methanol (140 mL) and treated with an excess of ammonium formate (1.64g, 25.0 mmol) followed by 10% palladium on carbon (410 mg). The resulting suspension was stirred at reflux for 1 hour. After cooling, the reaction mixture was filtered through a pad of celite. The filtrate was concentrated in vacuo to a brown oil (780 mg, 97%). NMR.

Preparation 8

(S)-4-[2-Hydroxy-3-aminopropoxy]benzimidazole

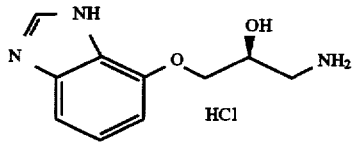

(S)-4-[2-(Dimethyl tert-butylsilyl)oxy-3-aminopropoxy] benzimidazole (10 mg, 31 mmol) was dissolved in THF (1 mL) and the mixture cooled to 0° C. Tetrabutylammonium fluoride (1 mL, 1.0 M solution in THF) was added. The reaction stirred at this temperature for 4 hours. The reaction was quenched by addition of water. Evaporation of the aqueous layer provided the desired alcohol. NMR. MS.

Preparation 9

(S)-3-(4-Amino-3-nitrophenoxy)-1,2-epoxypropane

A solution of 4-amino-3-nitrophenol (2.54 g, 16.5 mmol) and (2S)-(+)-glycidyl 3-nitrobenzenesulfonate (4.27 g, 16.5 mmol) in 50 mL of acetone was treated with 1.1 equivalents of $K_2CO_3$ (2.50 g, 18.1 mmol) and stirred at reflux for 20 hours. The suspension was cooled to ambient temperature, concentrated in vacuo to dryness. The resulting solids were partitioned between chloroform and water, and the aqueous layer extracted with chloroform. The organic layers were combined and dried over MgSO₄ and concentrated in vacuo to provide 3.0 g (87%) of an orange solid. TLC and NMR indicated >95% purity, so the material was used without further purification. NMR.

Preparation 10

(S)-[3-(N,N-Dibenzylamino)-2-hydroxypropoxy]-4-amino-3-nitrobenzene

The epoxide from preparation 9 (3.0 g, 14.3 mmol) was dissolved in 100 mL of methanol and treated with dibenzylamine (3.02 mL, 15.7 mmol). The mixture was stirred at reflux for 6 hours and, after cooling, the solvent was removed in vacuo. The resulting orange solid (5.8 g, 100%) was used without further purification. NMR.

Preparation 11

(S)-[3-(N,N-Dibenzylamino)-2-hydroxypropoxy]-3,4-diamino benzene

The nitroaniline from preparation 10 (4.89 g, 12.0 mmol) was suspended in a mixture of ethanol (400 mL) and water (300 mL) at ambient temperature and treated with sodium bicarbonate (12.1 g, 144 mmol, 12 equiv.) and sodium hydrosulfite (25.1 g, 144 mmol, 12 equiv.) The reaction mixture slowly became colorless over three hours. The reaction mixture was partitioned between chloroform and brine. The organic layer was washed several times with brine, dried over magnesium sulfate and concentrated in vacuo to give a brown oil. NMR.

Preparation 12

(S)-5-[2-Hydroxy-3-(N,N dibenzylamino)propoxy]-1,3-dihydro-2H-benzimidazol-2-one The diamine from Preparation 11 (2.1 g, 5.6 mmol) was suspended in a mixture of toluene (40 mL) and 2N HCl (70 mL) at ambient temperature with vigorous stirring. An excess of triphosgene (17.3 g, 58.3 mmol) was added. The stirring continued for 14 hours. The biphasic mixture was cautiously quenched and neutralized with sodium bicarbonate, which caused an off-white precipitate to form at the interface. The precipitate was filtered and dried in vacuo to yield 1.06 g (47%) of a grey solid that was used without further purification. TLC, NMR and MS all indicated high purity of the intermediate.

Preparation 13

(S)-5-[2-Hydroxy-3-amino)propoxy]-1,3-dihydro-2H-benzimidazol-2-one

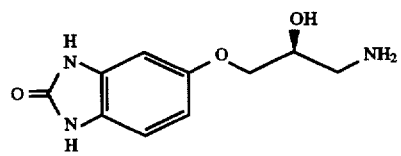

The compound from preparation 12 (0.75 g, 1.9 mmol) was dissolved in methanol (100 mL) and treated with an excess of ammonium formate (0.7 g, 11.2 mmol), followed by 10% palladium on carbon (400 mg). The suspension was stirred at reflux for 3 hours. After cooling the suspension, the reaction mixture was filtered through celite and the filtrate concentrated in vacuo to a greyish black solid (0.25 g, 60%). NMR. MS.

Preparation 14

(S)-5-[2-(Dimethyl tert-butylsilyl)oxy-3-(dibenzylamino) propoxy]benzimidazole

This compound was prepared in a manner analogous to Preparation 6. NMR. MS.

Preparation 15

(S)-5-(2-(Dimethyl-tert-butylsilyl)oxy-3-amino propoxy]-benzimidazole

This compound was prepared in a manner analogous to Preparation 7. NMR. MS.

Preparation 16

(S)-4-[2-Hydroxy-3-amino propoxy]benzimidazole

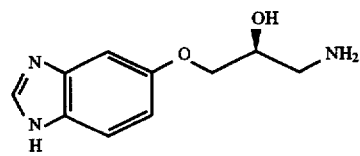

The desired aminoalcohol was prepared in a manner similar to Preparation 8. NMR. MS.

Preparation 17

4-[(2S)-2,-3-oxo-propoxy]-2(3H)benzoxazolone

A solution of 4-Hydroxy-2(3H)benzoxazolone (1.00 g, 6.6 mmol) and (2S)-(+)-glycidyl 3-nitrobenzenesulfonate (1.72 g, 6.6 mmol) in 50 mL of acetone was treated with 1.1 equivalents of K₂CO₃ (1.01 g, 7.3 mmol) and stirred at reflux for 4 hours. The suspension was cooled to ambient temperature, the solvent concentrated in vacuo to dryness. The resulting solids were partitioned between chloroform and water, and the aqueous layer extracted once with chloroform. The organic layers were combined and dried over Na₂SO₄ and concentrated in vacuo to give a white solid. Flash chromatography (chloroform/methanol 9/1) provided the monoalkylated product (0.55 g, 40%). NMR. MS.

Preparation 18

(S)-4-[2-Hydroxy-3-aminopropoxy]-2(3H) benzoxazolone

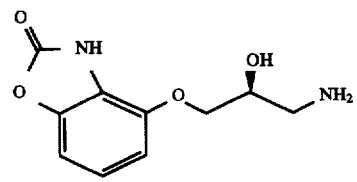

A solution of 4-[(2S)-2, 3-oxo-propoxy]-2(3H) benzoxazolone (0.15 g, 0.72 mmol) in methanol (2 mL) was cooled to −78° C. using a dry ice/acetone bath. Ammonia gas (2 mL) was condensed into the reaction mixture. The reaction vessel was capped and allowed to warm slowly to room temperature overnight. The reaction was quenched by uncapping the reaction vessel and allowing the ammonia gas to evaporate. NMR. MS.

Preparation 19

(S)-4-(4-[2-(N-[3-(2-amino-3-nitrophenoxy)-2-hydroxypropyl]amino)-2-methylpropyl]phenoxy) benzamide

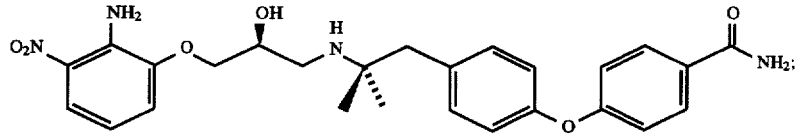

A suspension of (S)-3-(2-amino-3-nitrophenoxy)-1,2-epoxypropane (5 g, 23.8 mmol) and 4-(4-(2-amino-2-methylpropyl)phenoxy)benzamide (20.3 g 71.1 mmol) in absolute ethanol (200 mL) was heated to 550° C. for 12 h. All solids went into solution at 50° C. Upon completion of the reaction, the solvent was evaporated to dryness. The residue was redissolved in ethyl acetate and washed with a saturated solution of sodium bicarbonate. The layers were separated and the aqueous phase was extracted with ethyl acetate. The two organic layers were combined and washed with brine. The phases were separated and the organic layer was dried over sodium sulfate, filtered, and the solvent evaporated. Column chromatography eluting with 20% MeOH/CHCl$_3$ gave 7.26 g (62%) of product. NMR. MS.

Preparation 20

(S)-4-(4-[2-(N-[3-(2,3-diaminophenoxy)-2-hydroxypropyl]amino)-2-methylpropyl]phenoxy) benzamide

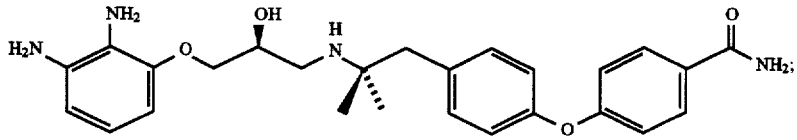

The nitroaniline from preparation 19 (0.484 g, 0.98 mmol) was dissolved in absolute ethanol (40 mL) and treated with a solution of sodium bicarbonate (0.50 g, 5.95 mmol) in water (10 mL) followed by a solution of sodium hydrosulfite (1.41 g, 8.1 mmol) in water (15 mL). Once the color had completely diminished, the solvents were evaporated. The residue was washed with water to remove excess salts. The leftover amorphous material was dissolved in methanol and gravity filtered. The solvent was evaporated to give 0.454 g (100%) of product. NMR. MS.

Preparation 21

4-t-butyldimethylsilyloxyindole

A solution of 4-hydroxyindole (3.0 g, 22.5 mmol), t-butyldimethylsilyl chloride (5.09 g, 33.8 mmol) and imidazole (3.83 g, 56.3 mmol) in dimethylformamide (60 mL) was stirred at room temperature for 24 hours. Aqueous ammonium chloride was added (100 ml) and extracted several times with ethyl acetate. The organic layers were combined, dried over magnesium sulfate, and evaporated to give a crude oil. Flash chromatography (10% ethyl acetate/hexanes) yielded the desired product (5.55 g, 100%) as a white solid. NMR.

Prepartion 22

4-t-butyldimethylsilyloxy-2-phenylindole
4-t-Butyldimethylsilyoxyindole (4.67g, 18.9 mmol) was dissolved in THF (100 ml) at −78° C. under a nitrogen atmosphere and treated with butyllithium (13.0 ml, 1.6 M in hexanes, 20.8 mmol) dropwise over 10 minutes. After stirring for 30 minutes, carbon dioxide gas was passed through the solution for 20 minutes. The clear solution was allowed to warm to room temperature and vigorous effervescence was observed. The excess carbon dioxide was removed under vacuum on a rotary evaporator at room temperature while the solvent was concentrated to an approximately 50 ml volume. Additional THF (60 mL) was added and the solution was cooled to −78° C. To this mixture, t-butyllithium (12.2 ml, 20.8 mmol) was added dropwise over 10 minutes, and the mixture stirred for 2h at −78° C. Tributyltin chloride (5.4 ml, 19.8 mmol) was added dropwise. After stirring for 1.5 h, the cold solution was poured over crushed ice-water (100g), and saturated ammonium chloride was added until solution became acidic. The aqueous solution was extracted with ether (3×100 ml), dried over magnesium sulfate, and concentrated to give 12.68 g of a yellow oil.

To a solution of this 1-carboxy-2-(tributylstannyl)indole (12.68g) in ethanol (100 ml) was added iodobenzene (2.1 ml, 18.9 mmol) and bis(triphenylphosphine)palladium(II) chloride (0.60 g, 0.85 mmol). The mixture was maintained at reflux for 48 h. The mixture was cooled to room temperature, filtered through a pad of celite, and concentrated at reduced pressure. Flash chromatography (5% ethyl acetate/hexanes) provided the 4-t-butyldimethylsilyloxy-2-phenylindole as a white solid. NMR. MS.

Preparation 23

4-hydroxy-2-phenylindole 4-t-Butyldimethylsilyoxy-2-phenylindole (55 mg, 0.17 mmol) was dissolved in THF (10 ml) at 0° C. and treated with tetrabutylammonium flouride (0.5 ml, 1.0 M in THF, excess). After stirring at this temperature for 10 minutes, the reaction was quenched by addition of saturated ammonium chloride. The mixture was extracted several time with ethyl acetate, dried over magnesium sulfate, and evaporated to give a crude oil. Flash chromatography (5% ethyl acetate/hexanes) provided the desired phenol (30 mg, 84.8%) as a white solid. NMR. MS.

Preparations 24 through 37 describe syntheses of compounds utilized in combinatorial/parallel scheme II.

Preparation 24

4-(3-oxobutyl)-1-(2-oxazolidine)benzene

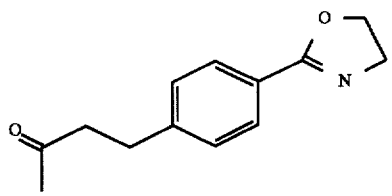

4-bromo-1-(2-oxazolidine)benzene (3.0 g, 13.3 mmol), 3-buten-2-ol (1.4 g, 20 mmol), Pd(OAc)2 (60 mg, 0.26 mmol), (o-tolyl)3P (158 mg, 0.52 mmol), sodium bicarbonate (1.34 g, 15.9 mmol) in 30 mL of N-methylpyrrolidinone was heated under nitrogen at 130° C. for 1 hour. The reaction mixture was then cooled and was partitioned between ethyl acetate and water. The combined organic layers were washed with water and then dried (Na₂SO₄), filtered and concentrated in vacuo to yield 2.6 g of a tan oil. Purification by flash chromatography (silica gel, 1:1 ethyl acetate/hexane) yielded 1.9 g of a pale yellow oil which crystallized upon drying under vacuum. Recrystallization from hexane gave 1.47 g (49%) of white needles, m.p. 62°–64° C. NMR. MS.

Preparation 24

4-[4-(3-oxobutyl)phenoxy]benzonitrile

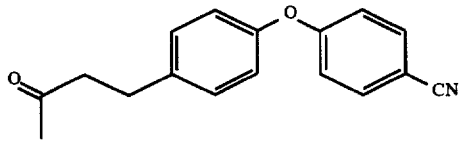

4-fluorobenzonitrile (6.05 g, 50mmol), 4-(4-hydroxyphenyl)-2-butanone (8.21 g, 50mmol) and potassium carbonate (8.3 g, 60mmol) were dissolved in N,N-dimethylacetamide (50 mL) and heated at 150° C. for 4 hours under nitrogen. The reaction mixture was then poured into 800 mL of ice water. A slowly crystallizing solid was filtered to give 13 g of crude product. This material was recrystallized from ethanol/water (3:1) to give 10.48 g (79%) of pale brown crystals, m.p. 64°–66° C. EA. NMR. MS.

Preparation 25

[4-(3-oxobutyl)phenoxy]benzamide

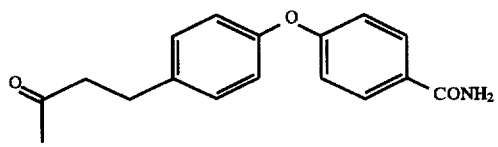

4-[4-(3-oxobutyl)phenoxy]benzonitrile (6.0 g, 22.6mmol) and potassium carbonate (1.0 g, 7.2mmol) were slurried in DMSO (50mL) and cooled to 0° C. in an ice bath. Aqueous 30% hydrogen peroxide (6 mL) was added slowly, and the mixture stirred at 0 C. for 1 hour. The reaction was quenched by pouring into 500 mL water, and the subsequent white precipitate was collected and washed with water. This material was recrystallized from 300 mL ethanol to give 5.35 g (84%) white crystals, m.p. 169°–1720° C. NMR. MS. EA.

Preparation 26

2-triphenylmethyl-5-chloromethyltetrazole

5-Chloromethyltetrazole (1.19 g, 10 mmol) in CH₂Cl₂ (10 mL) was treated with triphenylmethyl chloride (2.79 g, 10 mmol) and diisopropylethylamine (2.0 mL, 11.5 mmol) and stirred for 40 minutes at room temperature. The reaction mixture was concentrated in vacuo and partitioned between ethyl acetate/water. The organic layer was washed with saturated NaHCO₃ solution, then brine, dried (Na₂SO₄) and concentrated in vacuo to yield 3.48 g of an off-white solid. Trituration of this residue in diethyl ether yielded 3.04 g (84%) of a white solid, m.p.162°–165° C. NMR. MS. EA.

Preparation 27

5-[4-(2-oxobutyl)phenoxymethyl]tetrazole

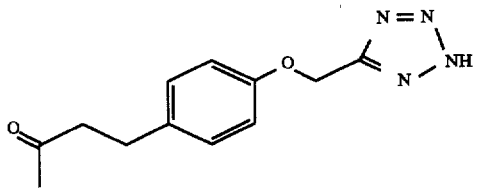

4-(4-hydroxyphenyl)-2-butanone (493 mg, 3 mmol) was cooled to 5° C. and treated with NaH (180 mg, 4.5 mmol, 60% in mineral oil) under nitrogen. After 15 minutes the ice bath was removed and the solution allowed to warm to room temperature over 45 minutes. The reaction was cooled to 5° C. and treated with 2-triphenylmethyl-5-chloromethyltetrazole (1.08 g, β₃ mmol) and stirred at room temperature for 3 hours. The reaction mixture was poured into EtOAc (300 mL), and washed with water then brine. The organic layer was dried (MgSO₄) and concentrated in vacuo to provide a yellow solid. This material was suspended in a mixture of MeOH (100 mL) and THF (50 mL) and treated with 4N HCl in dioxane (7.5 mL, 30 mmol). The resulting mixture was stirred for 1.5 hr. and then concentrated in vacuo to provide a tan solid. The residue was applied to a silica chromatography column and eluted with 33–100% ethyl acetate in hexane to provide 235 mg (32%) of a white solid, m.p.148°–150° C. NMR. MS. EA.

Preparation 28

3-[4-(2-oxobutyl)phenoxymethyl]pyridine

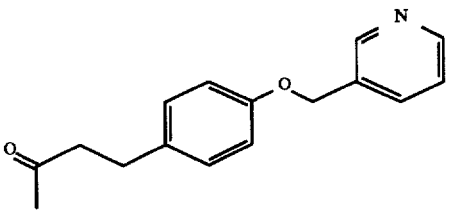

4-(4-hydroxyphenyl)-2-butanone (4.11 g, 25 mmol) and potassium carbonate (10.37 g, 75 mmol) in acetone (30 mL) was treated with 3-picolyl chloride hydrochloride (4.27 g, 26 mmol) under nitrogen. The mixture was stirred at reflux for 21 hours, proceeding about 50% towards completion. Potassium iodide (2.0 g, 13 mmol, 0.5 eq) was added and after 3 hours no picolyl chloride was observed on TLC. The volatiles were removed in vacuo and the resulting residue partitioned between EtOAc/water. The combined organic layers were washed with water, saturated NaHCO₃ solution, 10% Na₂SO₃, and then brine. The organic layer was dried (MgSO₄) and concentrated in vacuo to provide 4.8 g of a yellow oil. The material was purified on a Waters Prep 2000LC by elution with 10–80% ethyl acetate in hexanes over 45 minutes to yield 2.20 g (34%) of an oil which solidified on standing, m.p. 35°–370° C. NMR. MS. EA.

Preparation 29

2,6-dimethoxy-4-[4-(2-oxobutyl)phenoxy]-1,3,5-triazine

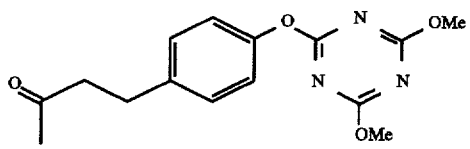

4-(4-hydroxyphenyl)-2-butanone (4.93 g, 30 mmol) was added to a solution of sodium methoxide (1.62 g, 30 mmol) in methanol (150 mL) under nitrogen. After stirring for 1 hour the methanol was removed in vacuo and the residue suspended in acetone (200 mL). The suspension was treated with 4,6-dimethoxy-2-chlorotriazine and refluxed for 3 hours. The volatiles were removed in vacuo and the residue partitioned between ethyl acetate/water. The organic layers were dried (MgSO4) and concentrated in vacuo to provide 10.28 g of a white semi-solid. The material was purified on a Waters Prep 2000LC by elution with a gradient of 20–60% ethyl acetate in hexanes over 55 minutes to yield 4.43 g (49%) of a colorless oil. NMR. MS. EA.

Preparation 30

2-[4-(2-oxobutyl)phenoxy]-5-carboxamidopyridine

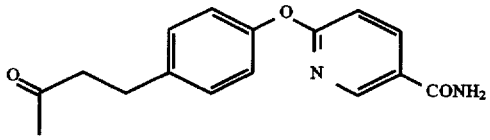

4-(4-hydroxyphenyl)-2-butanone (3.28 g, 20 mmol) in anhydrous DMF (150 mL) was treated with NaH (1.2 g, 30 mmol, 60% in mineral oil) under nitrogen. The solution was stirred for 30 minutes at ambient temperature and then treated with 6-chloronicotinamide (3.13 g, 20 mmol). The reaction was stirred at 60° C. for 1.5 hours and then 90° C. for five hours. The reaction was allowed to cool, poured into 50% saturated ammonium chloride solution, and extracted with EtOAc. The organic layer was dried (MgSO₄) and concentrated in vacuo with a xylene azeotrope to yield 11.4 g of a brown oil. The material was purified on a Waters Prep 2000LC by elution with 75–100% EtOAc over 60 minutes. The resulting material was triturated in cold EtOAc and collected by filtration to provide 2.73 g (48%) white solid m.p. 137°–1390° C. EA. NMR. MS.

Preparation 31

2-[4-(2-oxopropyl)phenoxy]-5-carboxamidopyridine

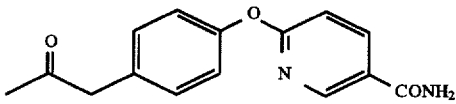

In a manner similar to the above examples, 3-(4-hydroxyphenyl)-2-propanone (2.25 g, 15 mmol) was treated with NaH (0.9 g, 22.5 mmol, 60% in mineral oil) followed by reaction with 6-chloronicotinamide (2.34 g, 15 mmol). Following workup the material was purified on a Waters Prep 2000LC to provide 1.28 g (32%) of a light yellow solid. m.p. 172°–1740° C. NMR. MS. EA.

Preparation 32

{4-[(2-oxocyclohexyl)methyl]phenyl}methanenitrile

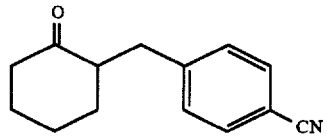

A mixture of methyl cyclohexanone-2-carboxylate (11.0 g, 70 mmol, from Fluka), α-bromo-p-tolunitrile (12.3 g, 63 mmol), potassium carbonate (10.5 g, 76 mmol) in THF (200 mL) was refluxed for 24 hours. The progress of the reaction was followed by GC. The reaction was diluted with water and the THF was removed under reduced pressure. The aqueous portion was extracted with EtOAc, dried (MgSO₄) to give 19.3 g of a white solid that was 74% pure by gas chromatrophy. The solid was recrystallized from hexane/EtOAc to give 7.75 g white crystals that were 100% pure by glc. A second crop of 3.65 g was obtained by adding more hexane to the filtrate. Overall, 11.4 g (67%) of 1-[(4-cyanophenyl)methyl]-1-methoxycarbonyl-2-oxocyclohexane carboxylate, was obtained; mp 82°–84° C. NMR. MS.

Under a blanket of nitrogen, a mixture of 1-[(4-cyanophenyl)methyl]-1-methoxycarbonyl-2-oxocyclohexane carboxylate (7.6 g, 28 mmol), sodium cyanide (2.1 g, 42 mmol) and DMSO (100 mL) was heated at 115° C. for 1.5 hours. The progress of the reaction was monitored by gc. The reaction was cooled and partitioned between water, EtOAc and brine. The organic layer was washed with water and dried (MgSO₄). After concentration, crude product was obtained as a tan oil. Purification by plug filtration (200 g silica gel, 15% EtOAc/hexane) gave 3.3 g (55%) product as colorless oil. NMR. MS.

Preparation 33

4-[(2-oxocyclohexyl)methyl]benzamide

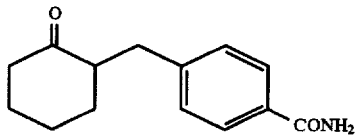

A DMSO (20 mL) solution of the compound of Preparation 28 (2.5 g, 11.7 mmol) was cooled in an ice bath. Solid

31

$K_2C_3$ (500 mg) was added followed immediately by 30% $H_2O_2$ (3 mL). After 20 minutes, TLC (3/7 EtOAc/hexane) showed a trace of starting material remained. The ice bath was removed and the reaction was stirred and room temperature for 1 hour. The reaction was diluted with 500 mL water and the white solid collected and dried to give 2.44 g (90%) desired amide. The product was recrystallized from 1/9 EtOAc/hexane to give 2.02 g of the titled product as white crystals, mp 167°–170° C. NMR. MS.

Preparation 34

2-Tetralone-6-carboxylic acid, ethylene ketal 6-bromo-2-tetralone (2.0 g, 8.89 mmol) was dissolved in toluene (50 mL) and treated with excess ethylene glycol (4.88 mL, 88.9 mmol) and catalytic p-toluenesulfonic acid (15 mg). The solution was stirred at reflux 16 hours, and water was removed from the reaction mixture using a Dean-Stark condenser. After cooling to ambient temperature, the toluene solution was washed 2×1N NaOH, 1 × water, 1 × brine, dried over $Na_2SO_4$ and concentrated in vacuo to give 2.23 g (93%) of 6-bromo-2-tetralone ethylene ketal as a brown oil which was used without further purification.

6-Bromo-2-tetralone ethylene ketal (2.2 g, 8.15 mmol) was dissolved in anhydrous THF (30 mL), cooled to −78° C. and treated with tert-butyllithium (12.05 mL, 20.4 mmol, 1.7M in pentane) under an atmosphere of nitrogen. After stirring for 30 minutes, anhydrous carbon dioxide gas was passed through the reaction mixture for 20 minutes at −78° C. The suspension was then allowed to warm to ambient temperature. The solution was quenched with water and acidified with 1N HCl, then extracted 2 × EtOAc. The organic extracts were washed with brine, dried over $Na_2SO_4$ and concentrated in vacuo to a pale brown oil. The oily residue was applied to a silica flash chromatography column and eluted with 30%–50% EtOAC in hexanes to yield tetralone-6-carboxylic acid, ethylene ketal 1.06 g (55%) of a slowly crystallizing solid. NMR. MS.

Preparation 35

2-Tetralone-6-carboxamide

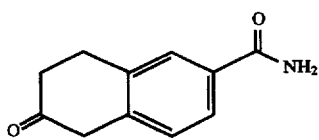

Tetralone-6-carboxylic acid, ethylene ketal (395 mg, 2.07 mmol) was co-dissolved in $CH_2Cl_2$ (50 mL) with N-hydroxysuccinimide (260 mg, 2.76 mmol) at 0° C. and treated with a slight excess of 1,3-dicyclohexylcarbodiimide (502 mg, 2.50 mmol). The mixture was allowed to warm to ambient temperature over 30 minutes, during which time a fine white precipitate formed. Ammonium chloride (333 mg, 6.23 mmol) and triethylamine (1.58 mL, 12.5 mmol, d=0.797) were added. The solution was stirred at ambient temperature for 16 hours. The suspended urea and salts were filtered away and the solution concentrated in vacuo to a colorless oil. The oil was applied to a silica flash chromatography column and eluted with 50–100% EtOAc in hexanes to yield 250 mg (64%) of 2-tetralone-6-carboxamide, ethylene ketal as a white solid, clean by NMR, TLC. 2-Tetralone-6-carboxamide ethylene ketal (250 mg, 1.07 mmol) and catalytic p-toluenesulfonic acid were stirred in acetone (50 mL) at ambient temperature for 48 hours. The volatiles were removed in vacuo and the residue triturated in ethyl acetate. The solids were filtered, washed and dried to yield 77.5 mg (38%) of 2-Tetralone-6-carboxamide as a white powder, pure by NMR, TLC. MS.

Preparation 36

2-Tetralone-6-morpholinamide

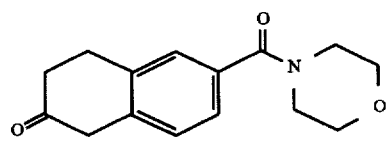

2-Tetralone-6-carboxylic acid, ethylene ketal (395 mg, 2.07 mmol) was codissolved in $CH_2Cl_2$ (50 mL) with N-hydroxysuccinimide (260 mg, 2.76 mmol) at 0° C. and treated with a slight excess of 1,3-dicyclohexylcarbodiimide (502 mg, 2.50 mmol). The mixture was allowed to warm to ambient temperature over 30 minutes, during which time a fine white precipitate formed. Morpholine (0.91 mL, 10.4 mmol, d=0.998) was added and the solution stirred at ambient temperature for 16 hours The suspended urea was filtered away and the solution concentrated in vacuo to a colorless oil. The oil was applied to a silica flash chromatography column and eluted with 50–100% EtOAc in hexanes to yield 323 mg (51%) of 2-tetralone-6-morpholinamide, ethylene ketal as a slowly crystallizing solid, clean by NMR, TLC.

2-Tetralone-6-morpholinamide, ethylene ketal (323 mg, 1.06 mmol) and catalytic p-toluenesulfonic acid were stirred in acetone (50 mL) at ambient temperature for 48 hours. TLC indicated a mixture of 2-tetralone-6-morpholinamide, ethylene ketal and desired product, so the solution was heated to reflux for 16 hours. The volatiles were removed in vacuo and the residue applied to a silica flash chromatography column and eluted with 50–100% EtOAc in hexanes to yield 27 mg (10%) of 2-tetralone-6-morpholinamide a slowly crystallizing solid, pure by NMR, TLC. MS.

Preparation 37

(R) 4-[2-Hydroxy-3-(N,N-dibenzylamino)propoxy]-1,3-dihydro-2H-benzimidazol-2-thione

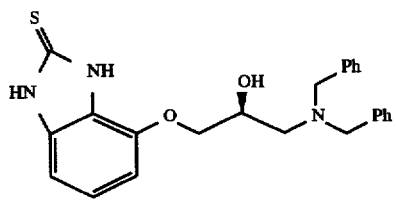

[3-(N,N-Dibenzylamino)-2hydroxypropoxy]-2,3-diamino benzene (400 mg, 1.1 mmol) was dissolved in a mixture of methylene chloride (70 mL) and pyridine (35mL) and cooled to 0OC. Dimethylamino pyridine (DMAP; 311mg, 2.5mmol) was added and thiophosgene (179mg, 0.119mL, 1.6mmol) was introduced in a dropwise fashion. After 30 minutes, another equivalent of thiophosgene was added and the mixture was stirred for 5 hours. Water was carefully added and the resulting biphasic mixture extracted with methylene chloride. The organic solution was dried over MgSO4 and, filtered and evaporated to leave a brown oil (445mg, ca. 100%). MS, NMR.

The above titled compound is converted to the amine for reaction in accordance with Scheme 1 by techniques appreciated in the art.

Preparation 38

4-(2-Methyl-2-nitropropyl)phenol

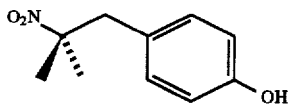

A mixture of 4-hydroxybenzyl alcohol (100.08 g, 806 mmol), 2-nitropropane (400 mL, 4.45 mol) and diglyme (800 mL) was heated to 38° C. Potassium t-butoxide (45.29 g, 403.6 mmol) was added, and the mixture was heated to reflux at 132° C. with a Dean-Stark trap. Water began collecting in the trap, and continued at a high rate for approximately 1.5 h. When water collection slowed (around 2.5 h) then portions of solvent (30–40 mL each) were removed every thirty minutes. During the water collection and solvent removal the temperature rose from 132° C. to 149° C. After 4 h less than 1% of the 4-hydroxybenzyl alcohol remained by HPLC analysis. The heating mantle was removed, and the reaction mixture was allowed to cool. When the temperature was 100° C. water (200 mL) was added, and the solution was allowed to cool to room temperature. Solvent was removed on a rotary evaporator under vacuum until 593 g of solution remained. Water (500 mL) and EtOAc (500 mL) were added and the layers were separated (layer separation was poor, but addition of 20% aqueous NaCl was ineffectual). The aqueous layer was extracted with EtOAc (200 mL), and the combined organic layers were extracted with 1N HCl (500 mL) and water (300 mL). The organic layer was distilled in vacuo to 261 g of oil to which EtOAc was added (160 mL). Heptane (3.4 L) was added rapidly with vigorous stirring for 30 min, and the product crystallized to yield a beige solid (112.36 g, 71% yield, >98% purity by HPLC analysis). Another crop of crystals may be obtained from the filtrate by concentrating and filtering the solids, or by concentrating more fully to a solution and adding heptane to crystallize. NMR. E.A.

Preparation 39

4-(2-amino-2-methylpropyl)phenol acetic acid salt

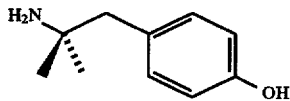

A one-gallon high-pressure reactor was charged with 4(2-methyl-2-nitropropyl)phenol (120 g, 614 mmol), HOAc (35.2 mL, 614 mmol), 5% Palladium on carbon (24 g) wetted with 2Bβ3 EtOH (60 mL), and MeOH (1230 mL). The mixture was heated to 50° C. with agitation (600 rpm), and the reactor was purged with $N_2$ and pressurized to 50 psi with $H_2$. After 15.5 h the reactor was purged with $N_2$, and the cooled mixture was filtered. The filter cake was washed with MeOH and the filtrate was concentrated to 514 g of slurry on a rotary evaporator. To this slurry was added EtOAc (2 L) with vigorous agitation. After stirring for 1 h, the resulting crystals were filtered and washed with a small amount of EtOAc. The product was dried overnight in a 45° C. vacuum oven to yield 118.83 g (86%) of product as small white needles (mp 211°–216° C. dec). This material was 99% pure by HPLC analysis, and while another 9.00 g of material was obtained from the mother liquor it was found to be only 88 % pure.

Preparation 40

2-(4-(2-amino-2-methylpropyl)phenoxy)-5-carboxamidopyridine

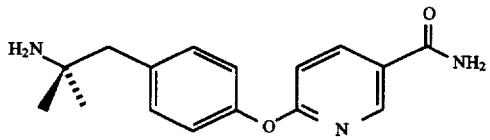

A mixture of 4-(2-amino-2-methylpropyl)phenol acetic acid salt (45.06 g, 200 mmol), powdered $K_2CO_3$ (69.1 g, 500 mmol), 6-chloronicotinamide (31.32 g, 200 mmol), DMAC (622 mL) and iso-octane (70 mL) was slowly heated to reflux at 140° C. A water trap filled with iso-octane was used to collect water formed in the reaction, and reflux was maintained for 5.5 h. The mixture was allowed to cool to room temperature, and the solids were filtered and washed with EtOAc. The filtrate was concentrated in vacuo to 88.6 g of solid which was dissolved in EtOAc (500 mL). To this solution was added water (800 mL), 1N HCl (200 mL) and MeOH (50 mL). The pH of this mixture was adjusted to 7.2 with con. HCl, and the aqueous layer was separated and washed with methyl t-butyl ether (500 mL). The product was crystallized by addition of 10N NaOH (20 mL) which raised the pH to 11. This pH was maintained by addition of 10N NaOH as needed during the course of the crystallization (90 min). The product was filtered, washed with water and dried in vacuo at 45° C. to 53.11 g (93%) of white solid which was >98% pure by HPLC analysis: H NMR (300 MHz, DMSO-$d_6$) NMR was consistent with the desired product;

Preparation 41

4-(4-(2-amino-2-methylpropyl)phenoxy)benzonitrile

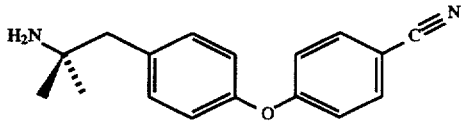

A mixture of 4-(2-amino-2-methylpropyl)phenol acetic acid salt (45.06 g, 200 mmol), powdered $K_2CO_3$ (69.1 g, 500 mmol), and DMAC (550 mL) was heated to 75°–100° C. Toluene (166 mL) was added, and the mixture was slowly heated to reflux at 134° C. The reflux temperature was raised by distillation of toluene and water into a water trap until the temperature reached 141° C. The mixture was then allowed to cool to below 100° C. at which point 4-fluorobenzonitrile (24.46 g, 202 mmol) was added along with 50 mL of toluene. The mixture was again heated to reflux at 140° C. with water being collected in a toluene-filled water trap for 4 h. The mixture was allowed to cool to room temperature, and the solids were filtered and rinsed with toluene. The filtrate was concentrated on a rotary evaporator to 77 g of syrup which was dissolved in EtOAc (400 mL). This solu-

Preparation 42

4-(4-(2-amino-2-methylpropyl)phenoxy)benzamide

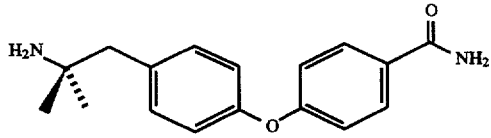

Aqueous 30% H$_2$O$_2$ (62.1 mL, 548 mmol) was added dropwise to a mixture of 4-(4-(2-amino-2-methylpropyl)phenoxy)-benzonitrile (53.2 g, 200 mmol), K$_2$CO$_3$ (15.78 g, 114 mmol) and DMSO (270 mL) over 20 min while the temperature was held at 20° C. with a cooling bath. The mixture was stirred at this temperature for 1 h after the addition was complete, and then water (209 mL) was added slowly. The slurry was cooled in an ice bath with stirring for 1 h, and the product was then filtered, washed with water and dried in vacuo at 50° C. to yield 55.0 g (97%) of white solid. Analysis by HPLC indicated purity of >99%: $^1$H NMR (300 MHz, DMSO-d$_6$) NMR was consistent with the desired product;

Preparation 43

2-(4-(2-amino-2-methylpropyl)phenoxy)-5-carbonitrilepyridine

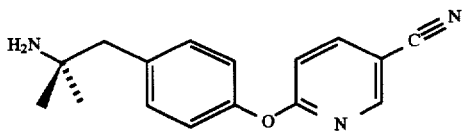

A mixture of 4-(2-amino-2-methylpropyl)phenol acetic acid salt (22.53g, 100 mmol), powdered K$_2$CO$_3$ (34.55 g, 250 mmol) and DMAC (275 ml) was heated to 100° C. Toluene (94 ml) was added and the mixture slowly heated to reflux. The reflux temperature was raised by distillation of toluene and water until it reached 140° C. The mixture was then cooled to below 100° C. and 2-chloronicotinonitrile (13.86g, 100 mmol) added with a toluene rinse (50 ml). The mixture was again heated to reflux and the reflux temperature raised to 140° C. as before. Then the water trap was filled with toluene and the reflux continued for 40 min., at which point an HPLC showed no 2-chloronicotinonitrile remained but the reaction was not complete. After cooling the reaction below reflux, additional 2-chloronicotinonitrile (0.63 g, 4.5 mmol) was added and reflux continued for 90 min. The reaction was cooled to room temperature and the solids filtered with a toluene wash. The filtrate was concentrated on a rotary evaporator to 41 g of syrup which was dissolved in EtOAc (200 ml). This solution was washed with water (200 ml) and the aqueous layer back-extracted with EtOAc (50 ml). The combined organic layers were washed with water (3×200 ml) and concentrated in vacuo to 26.93 g of solid, ~100% of theory. HPLC indicated 94.3% purity. H NMR (300 MHz, DMSO-d$_6$) was consistent with the desired product;

The following compounds were prepared in a manner analogous to schemes IV and/or preparations 24 through 33 described herein or by techniques appreciated in the art:

| Name | Structure | m.p. | Yield | Confirmed NMR | M.S. |
|---|---|---|---|---|---|
| (4-(3-oxobutyl)phenyl)methanenitrile Preparation 44 | 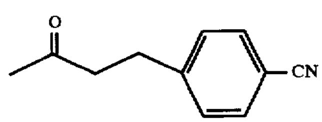 | oil | 33% | x | x |
| (3-(3-oxobutyl)phenyl)methanenitrile Preparation 45 | 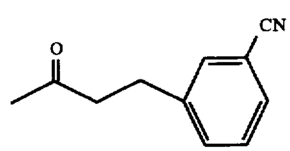 | oil | 44% | x | x |
| (3-(3-oxobutyl)benzamide Preparation 46 | 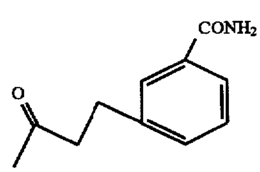 | 104–6 | 45% | x | x |
| (2-(3-oxobutyl)phenyl)methanenitrile Preparation 47 | 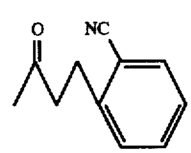 | oil | 43% | x | x |

-continued

| Name | Structure | m.p. | Yield | Confirmed NMR | M.S. |
|---|---|---|---|---|---|
| (2-(3-oxobutyl) benzamide Preparation 48 | 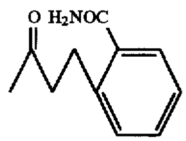 | 113–114 | 91% | x | x |
| (4-(3-oxohexyl) phenyl)methanenitrile Preparation 49 | 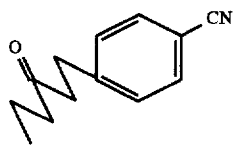 | oil | 85% | x | x |
| 4-(3-oxohexyl) benzamide Preparation 50 | 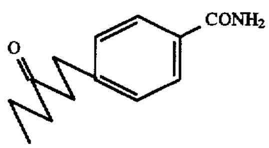 | 90–93 | 67% | x | x |
| 3-methyl-5-(4-3-oxobutyl)phenyl)-1H-tetrazole Preparation 51 | 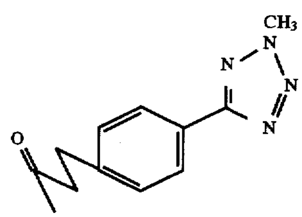 | 90–93 | 67% | x | x |
| (4-(3-oxobutyl)phenyl) sulfonamide Preparation 52 | 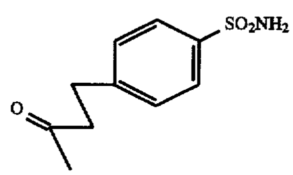 | 132-4 | 36% | x | x |
| (4-(1-methyl-3-oxobutyl)phenyl) methanenitrile Preparation 53 | 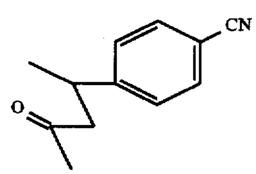 | oil | 44% | x | x |
| 3-benzyl-5-(4-(3-oxobutyl)phenyl)-1H-tetrazole Preparation 54 | 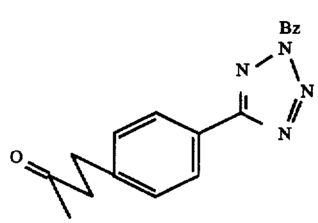 | 66–9 | 41% | x | x |
| 4-(1-methyl-3-oxobutyl)benzamide Preparation 55 | 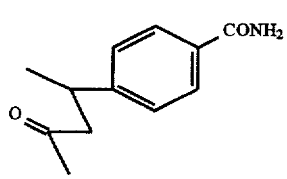 | 127–9 | 95% | x | x |

-continued

| Name | Structure | m.p. | Yield | Confirmed NMR | M.S. |
|---|---|---|---|---|---|
| 5-(4-(3-oxobutyl)phenyl)-1H-tetrazole Preparation 56 | 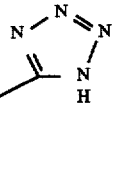 | 197–9 | 94% | x | x |
| 5-(3-oxobutyl)-2-furanoic acid Preparation 57 | 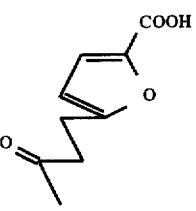 | 129–32 | 86% | x | x |
| 3-(2-fluoro-4-(3-oxobutyl)phenyl)propenoic acid Preparation 58 | 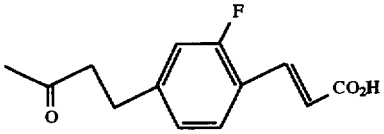 | 143–6 | 95% | x | x |
| (4-(3-oxobutyl)phenyl)ethanenitrile Preparation 59 | 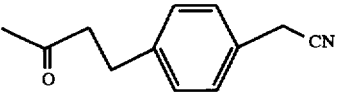 | oil | 100% | x | x |
| (4-(3-oxobutyl)phenyl)thioamide Preparation 60 | 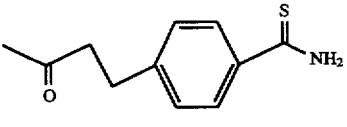 | 96–8 | low* | x | x |
| (2-fluoro-4-(3-oxobutyl)phenyl)methanenitrile Preparation 61 | 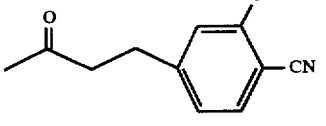 | oil | 78% | x | x |
| 2-fluoro-4-(3-oxobutyl)benzamide Preparation 62 | 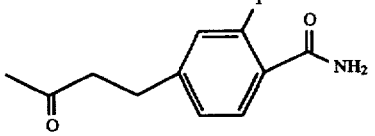 | 150–3 | 85% | x | x |
| 3-methyl-5-(2-3-oxobutenyl)phenyl-1N-tetrazole Preparation 63 | 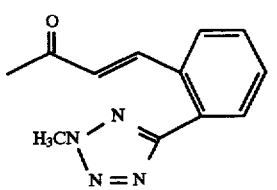 | 64–5 | 45% | x | x |
| (4-(3-oxocyclohexyl)phenyl)methanenitrile Preparation 64 | 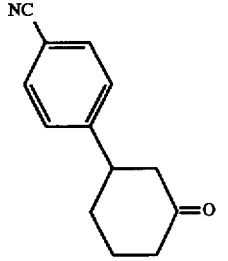 | 66–69 | 36% | x | x |

-continued

| Name | Structure | m.p. | Yield | Confirmed NMR | M.S. |
|---|---|---|---|---|---|
| 1-methyl-5-(2-(3-oxo-butenyl)phenyl)-1H-tetrazole Preparation 65 | 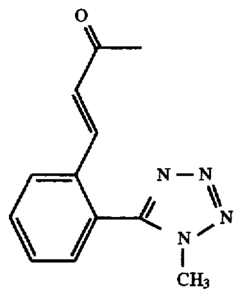 | 100–101 | 18% | x | x |
| (2,6-difluoro-(4-3-oxobutyl)phenyl))sulfonamide Preparation 66 | 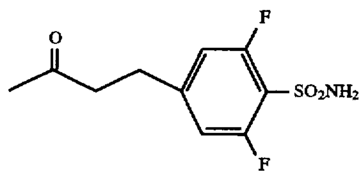 | oil | 41% | x | x |
| N-methoxyl-4-(3-oxobutyl)benzamide Preparation 67 | 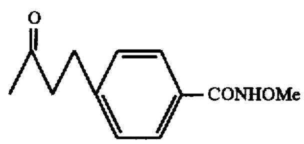 | | low | x | x |
| (4-(2-methyl-3-oxobutyl)phenylmethane nitrile Preparation 68 | 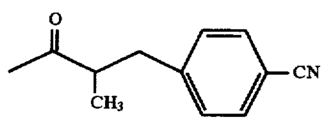 | oil | 66% | x | x |
| (4-(2-methyl-3-oxobutyl)benzamide Preparation 69 | 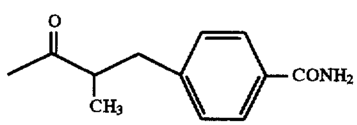 | 112–115 | 87% | x | x |
| (1-methyl-2-(4-(3-oxobutyl)phenyl)-4-trifluoromethyl)imidazole Preparation 70 | 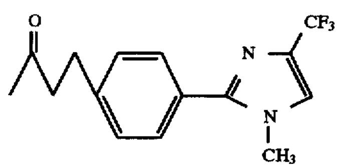 | 62–3 | 68% | x | x |
| 4-(1-2-dimethyl-3-oxobutyl)benzamide Preparation 71 | 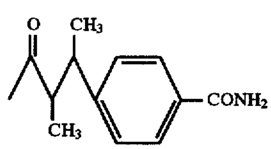 | 100–102 | 90% | x | x |
| 4-(3-oxocyclohexyl benzamide Preparation 72 | 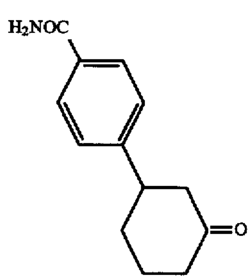 | 188–91 | 42% | x | x |
| 5-(3-oxobutyl)-2-thiophene sulfonamide Preparation 73 | 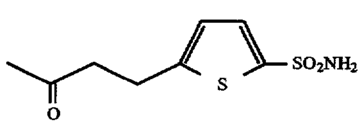 | 96–98 | 66% | x | x |

-continued

| Name | Structure | m.p. | Yield | Confirmed NMR | M.S. |
|---|---|---|---|---|---|
| (3-(3-oxobutyl)phenyl sulfonamide Preparation 74 | 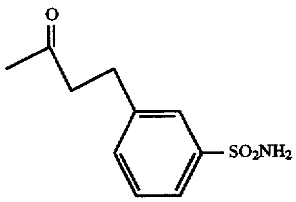 | 87–90 | 35% | x | x |
| 2-methyl-5-(3-(3-oxobutyl)phenoxy) phenyl)tetrazole Preparation 75 | 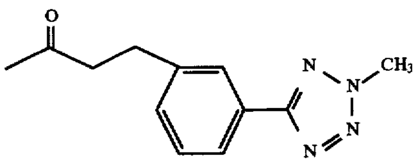 | 98 | 65% | x | x |
| 4-(3-oxocyclopentyl) benzamide Preparation 76 | 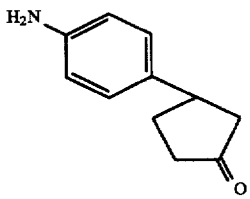 | 203–4 | 43% | x | x |
| 4-(1,1-dimethyl-3-oxobutyl)benzamide Preparation 77 | 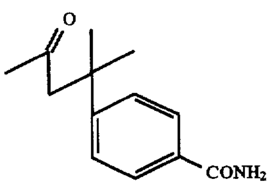 | 106–8 | 61% | x | x |
| (4-(3-oxocycloheptyl) phenyl)methanenitrile Preparation 78 | 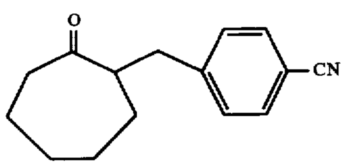 | oil | 54% | x | x |
| (4-(3-oxohexyl)phenyl) methanenitrile Preparation 79 | 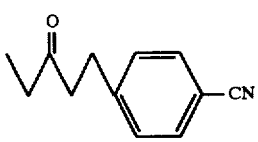 | oil | 77% | x | x |
| 4-(3-oxobutyl)-phthalhydrazide Preparation 80 | 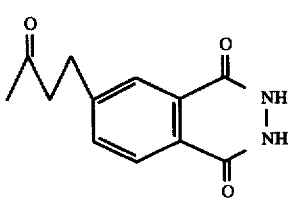 | 161–4 | 13% | x | x |
| 4-(3-oxohexyl) benzamide Preparation 81 | 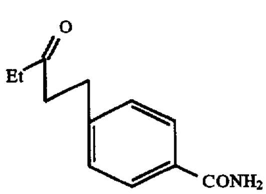 | 158–61 | 82% | x | x |

Note: The Preparation 76 structure shows an H₂N group, which may be a labeling inconsistency with the name "4-(3-oxocyclopentyl)benzamide".

-continued

| Name | Structure | m.p. | Yield | Confirmed NMR | M.S. |
|---|---|---|---|---|---|
| (4-(2,2-dimethyl-3-oxobutyl)phenyl) methanenitrile Preparation 82 | 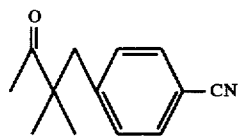 | oil | 72% | x | x |
| (4-(2,2-dimethyl-3-oxobutyl)benzamide Preparation 83 | 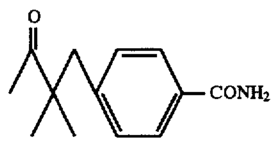 | 127–131 | 62% | x | x |
| 5-(2-methyl-3-oxobutyl)-2-thiophene sulfonamide Preparation 84 | 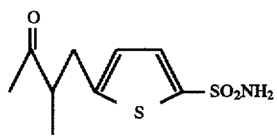 | oil | low | x | x |
| 4-((2-oxocycloheptyl)methyl)benzamide Preparation 85 | 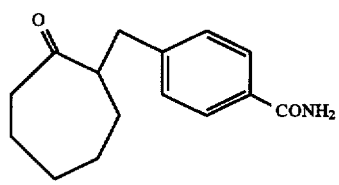 | 132–4 | 88% | x | x |
| (4-((2-oxocyclopentyl)methyl)phenyl methanenitrile Preparation 86 | 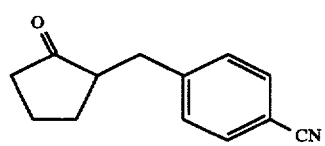 | oil | 62% | x | x |
| (4-((2-oxocyclopentyl)methyl)benzamide Preparation 87 | 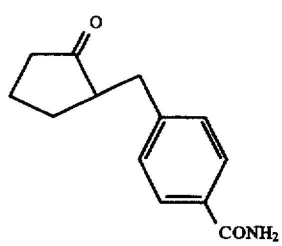 | 138–142 | 81% | x | x |
| (4-(4-(3-oxobutyl)phenoxy)methylphenyl) methanenitrile Preparation 88 | 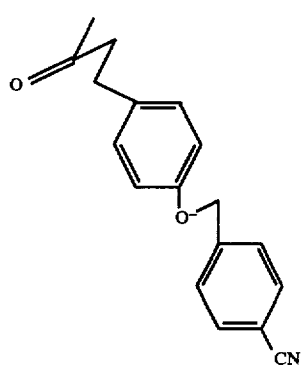 | 94–7 | 84% | x | x |

-continued

| Name | Structure | m.p. | Yield | Confirmed NMR | M.S. |
|------|-----------|------|-------|-----|------|
| 4-(4-(3-oxobutyl) phenoxy)methyl benzamide Preparation 89 | 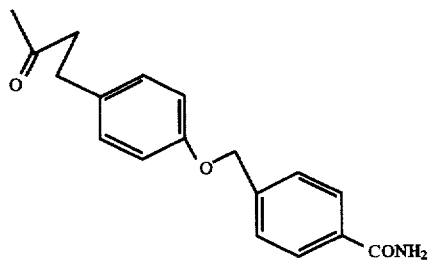 | 215–17 | 95% | x | x |
| (2-fluoro-4-(2-methyl-3-oxobutyl)phenyl) methanenitrile Preparation 90 | 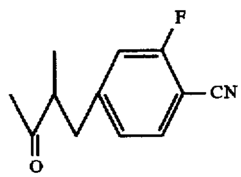 | oil | 42% | x | x |
| 2-fluoro-4-(2-methyl-3-oxobutyl)benzamide Preparation 91 | 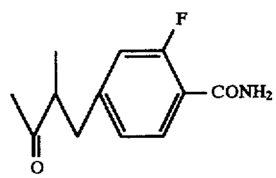 | 112–15 | 93% | x | x |
| 5-(2-fluoro-4-(2-methyl-3-oxobutyl) phenyl)-1H-tetrazole Preparation 92 | 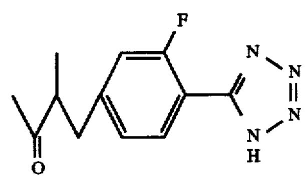 | 175–8 | 32% | x | x |
| 5-(3-oxobutyl)-2-(morpholinosulfonyl)-) thiophene Preparation 93 | 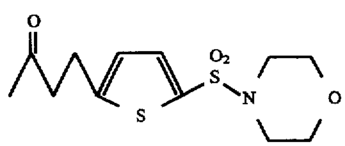 | 80–83 | 69% | x | x |
| 5-(2-methyl-3-oxobutyl)-2-(morpholinosulfonyl)-thiophene Preparation 94 | 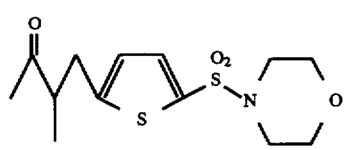 | oil | 15% | x | x |
| (4-(2-(4-(3-oxobutyl)phenoxy) ethyl)phenyl) methanenitrile Preparation 95 | 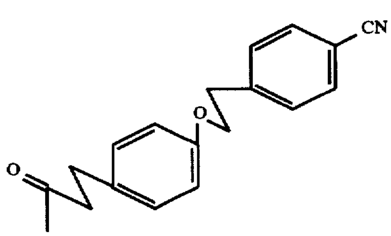 | oil | 41% | x | |

-continued

| Name | Structure | m.p. | Yield | Confirmed NMR | M.S. |
|---|---|---|---|---|---|
| (4-(4-(3-oxobutyl)phenyl)phenyl)methanenitrile Preparation 96 | 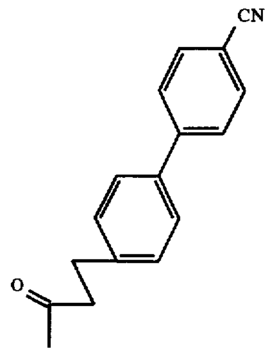 | 133–5 | 62% | x | x |
| (2-methyl-4-(3-3-oxobutyl)phenyl)methanenitrile Preparation 97 | 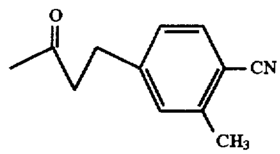 | oil | 55% | x | x |
| 4-(4-(3-oxobutyl)phenyl)benzamide Preparation 98 | 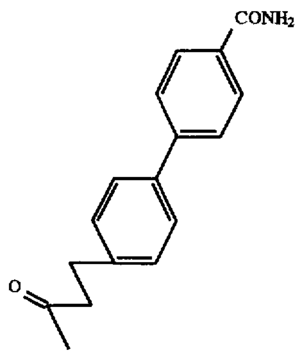 | 229–31 | 94% | x | x |
| (3-methyl-4-(3-oxobutyl)phenyl)methanenitrile Preparation 99 | 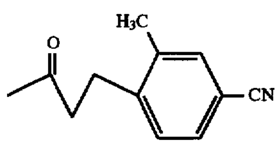 | 34–6 | 75% | x | x |
| 2-methyl-4-(3-oxobutyl)benzamide Preparation 100 | 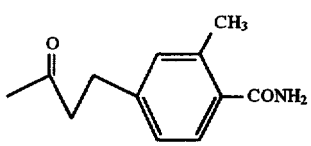 | 147–50 | 39% | x | x |
| 3-methyl-4-(3-oxobutyl)benzamide Preparation 101 | 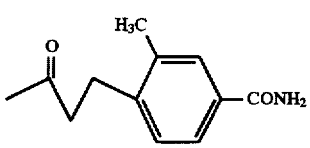 | 103–5 | 46% | x | x |
| 4-(2-(4-(3-oxobutyl)phenoxy)ethyl)benzamide Preparation 102 | 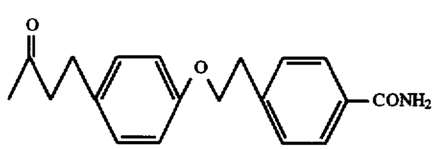 | semi-solid | 17% | x | x |
| 4-(4-oxopentyl)phenyl)methanenitrile Preparation 103 | 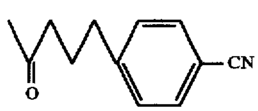 | oil | quant | x | x |

-continued

| Name | Structure | m.p. | Yield | Confirmed NMR | M.S. |
|---|---|---|---|---|---|
| 4-(4-oxopentyl)benzamide Preparation 104 | 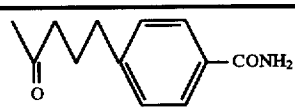 | 111–13 | 87% | x | x |
| (3-methyl-4-(2-methyl-3-oxobutyl)phenyl)methanenitrile Preparation 105 | 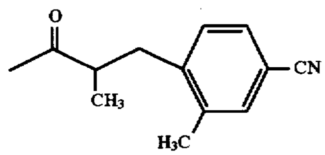 | oil | 64% | x | x |
| (3-methyl-4-(2-methyl-3-oxobutyl)benzamide Preparation 106 | 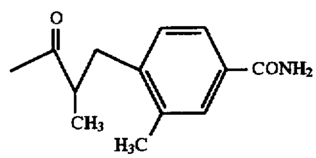 | 105–7 | 71% | x | x |
| (4-(2,5-dimethyl-4-(3-oxobutyl)phenoxy)phenyl)methanenitrile Preparation 107 | 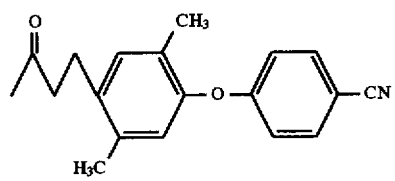 | 57–9 | low | x | x |
| (4-(2-ethyl-3-oxobutyl)benzoic acid Preparation 108 | 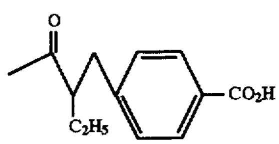 | 126–9 | 24% | x | x |
| (4-(2,5-dimethyl-(3-oxobutyl)phenoxy)benzamide Preparation 109 | 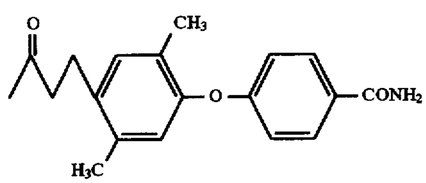 | 191–3 | 76% | x | x |
| (4-2,6-dimethyl-(3-oxobutyl)phenoxy)phenyl)methanenitrile Preparation 110 | 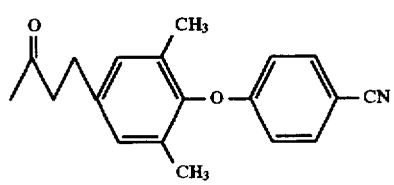 | yellow oil | 72% | x | x |
| (4-2,6-dimethyl-(3-oxobutyl)phenoxy)benzamide Preparation 111 | 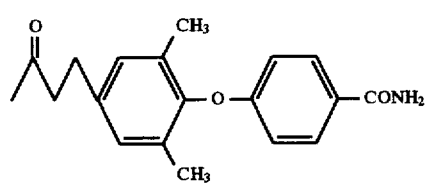 | 238–41 | 63% | x | x |

Example 1 is a combinatorial/parallel method for preparing compounds of the present invention in matrix fashion.

Example 1

A 5×8 grid of 4 mL screw cap vials was arranged. To each of the eight rows of vials in the grid was added 33 µmol of ketone (from preparations 24–37, 44–111, or commercially available), one ketone per row, as a stock solution in methanol (0.5M, 65 µl). If solubility was a problem, acetonitrile/methanol or DMF was used. To each column of vials in the grid was added 50 umol of amine hydrochloride, one amine hydrochloride (or amine) (from preparations 1 through 16, or commercially available) per column, as a stock solution in methanol (0.5M, 100 µl). To each vial was then added resin VIII (18–20 mg), 1.01 meq/g, 70–90µeq base). Teflon lined caps were then placed on each vial. The slurries were then shaken for 24 hours, at which time each vial was treated with approximately 30 mg (2.5 mmol $BH_4^-$/g resin, 75 µmol) of Amberlite IRA400 borohydride resin (Aldrich Chemical). The caps were replaced, and the vials were shaken for an additional 24 hours, then 150 µl methylene chloride and 40 mg (1 mmol/g resin, 0.4 mmol) polystyrene-linked benzaldehyde resin (Frechet, J. M.; Schuerch, C. J. *Am. Chem. Soc.* 1971, 93, 492.) in order to scavenge excess primary amine starting material were added to the vial, and the slurry was shaken for 1 day. Each vial was then filtered through a cotton plug. The residual resin was rinsed with three small portions of methanol (approximately 200 µl). The resulting solutions were then treated with 20µl of conc. HCl (120 µmol) to ensure formation of the HCl salt of the product amine, then each vial was diluted to a volume of approximately 4 mL, and 1 mL of each solution was transferred to a tared 4 mL screw cap vial. This solution was allowed to evaporate in a fume hood under an air stream until dry, then placed in a vacuum oven for 24 hours at room temperature. The resulting residues were then weighed and submitted directly for testing with no further purification. The bulk of the material (75%) was similarly evaporated.

The following matrices list additional examples 2–201. These compounds were prepared using combinatorial/ parallel techniques in accordance with the present invention. A1 l reaction conditions were the same from plate to plate and in substantial accordance with Scheme 2 and Example 1. The scaffold for each plate was the same and is depicted at the top corner of the 5×8 matrix. The variable functional groups are illustrated in the rows and columns. The ketones and the amines depicted on each plate were prepared in accordance with the schemes and preparations described herein or by techniques known in the art.

| R' = | R'' = | | | | | | |
|---|---|---|---|---|---|---|---|
| | (phthalhydrazide-alkyl) | (CONH₂-benzyl-cyclohexyl) | (H₂NOC-diphenyl ether-alkyl) | (SO₂NH₂-thiophene-alkyl) | (CONH₂-pyridyl-O-phenyl-alkyl) | (CONH₂-methylphenyl-alkyl) | (CONH₂-phenyl-cyclohexyl) |
| (benzimidazolone-O-ethyl) | Example 2 | Example 3 | Example 4 | Example 5 | Example 6 | Example 7 | Example 8 | Example 9 |
| (benzimidazolone-O-ethyl isomer) | Example 10 | Example 11 | Example 12 | Example 13 | Example 14 | Example 15 | Example 16 | Example 17 |
| (benzimidazole-O-ethyl) | Example 18 | Example 19 | Example 20 | Example 21 | Example 22 | Example 23 | Example 24 | Example 25 |
| (benzimidazole-O-ethyl isomer) | Example 26 | Example 27 | Example 28 | Example 29 | Example 30 | Example 31 | Example 32 | Example 33 |
| (N-methyl benzimidazolone-O-ethyl) | Example 34 | Example 35 | Example 36 | Example 37 | Example 38 | Example 39 | Example 40 | Example 41 |

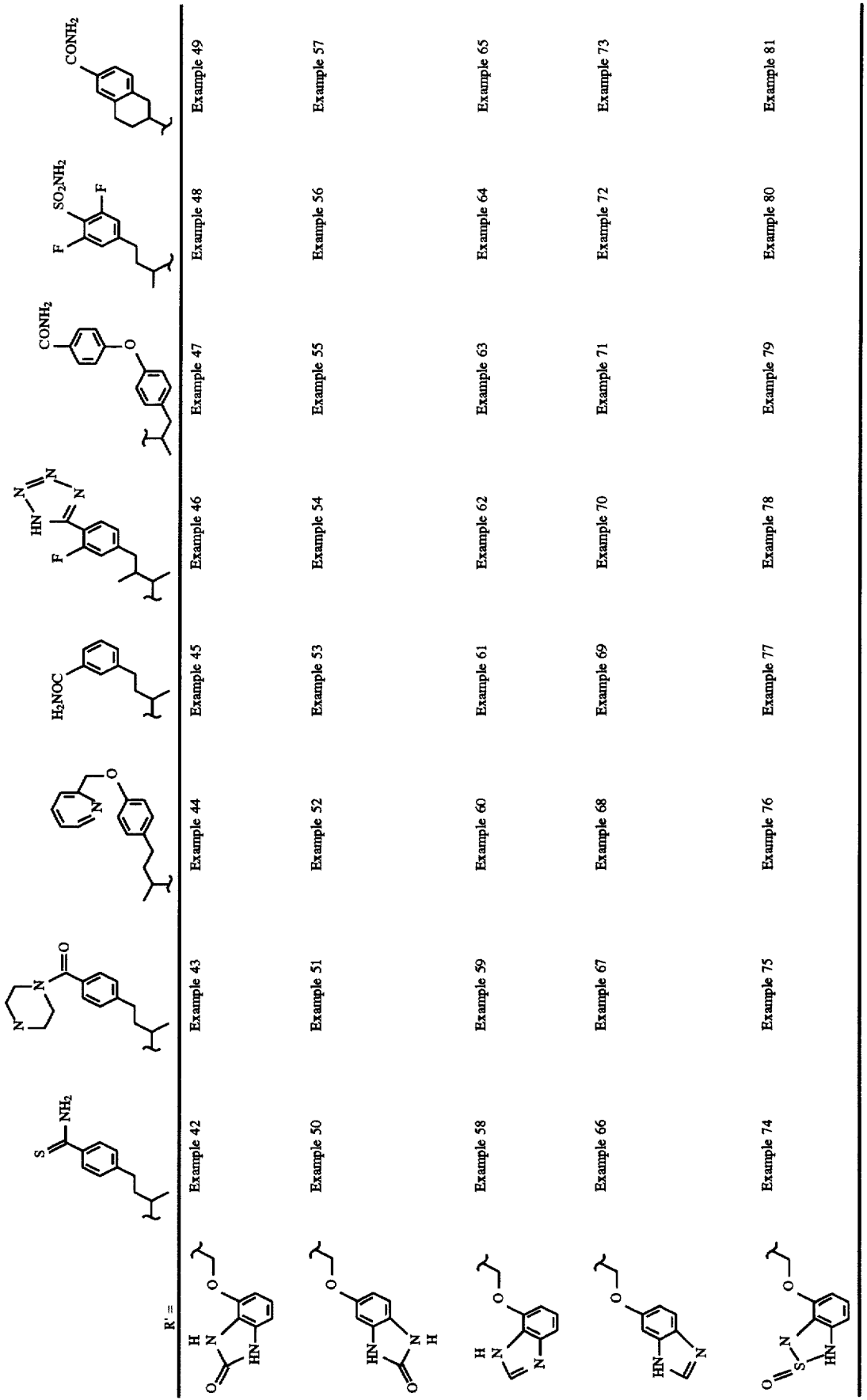

| R' = | R" = | | | | | | |
|---|---|---|---|---|---|---|---|
| | CONH-biphenyl-CH2CH(CH3)- | CONH2-phenyl-CH2-cyclopentyl | H2NOC-pyridyl-O-phenyl-CH2CH(CH3)- | morpholine-SO2-thiophene-CH2CH(CH3)- | CONH2-dimethylphenyl-CH2CH(CH3)- | H2NOC-phenyl-CH2O-phenyl-CH2CH(CH3)- | CONH2-phenyl-CH2CH(CH3)CH(CH3)- | CONH2-phenyl-CH2-cyclopentyl |
| benzimidazolone-O-CH2CH2- | Example 82 | Example 83 | Example 84 | Example 85 | Example 86 | Example 87 | Example 88 | Example 89 |
| benzoxazolone-O-CH2CH2- | Example 90 | Example 91 | Example 92 | Example 93 | Example 94 | Example 95 | Example 96 | Example 97 |
| benzoxazolone-O-CH2CH2- (isomer) | Example 98 | Example 99 | Example 100 | Example 101 | Example 102 | Example 103 | Example 104 | Example 105 |
| benzimidazole-O-CH2CH2- | Example 106 | Example 107 | Example 108 | Example 109 | Example 110 | Example 111 | Example 112 | Example 113 |
| N-methyl benzimidazolone-O-CH2CH2- | Example 114 | Example 115 | Example 116 | Example 117 | Example 118 | Example 119 | Example 120 | Example 121 |

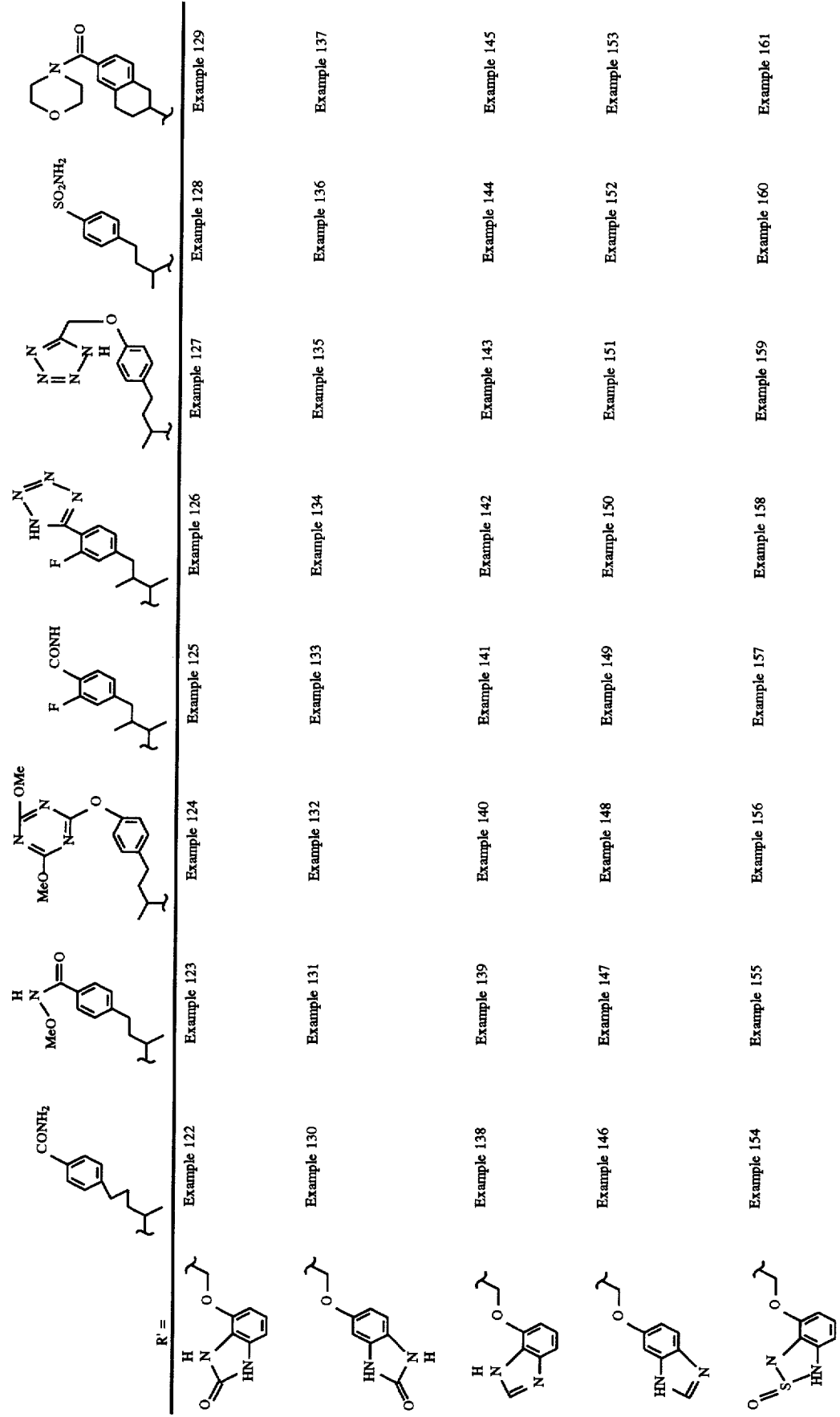

-continued

| R' = | R" = | | | | | | | |
|---|---|---|---|---|---|---|---|---|
| | CONH₂ (branched alkyl-phenyl) | CONH₂ (cyclohexyl-CH₂-phenyl) | HO₂C-phenyl-O-phenyl-alkyl | SO₂NH₂ (thiophene-alkyl) | CONH₂ (phenyl-alkyl) | MeOHNOC-phenyl-O-phenyl-alkyl | CN (cyclohexyl-phenyl) | CONH₂ (cyclohexyl-phenyl) |
| benzimidazolone-O-alkyl | Example 162 | Example 163 | Example 164 | Example 165 | Example 166 | Example 167 | Example 168 | Example 169 |
| benzimidazolone-O-alkyl (isomer) | Example 170 | Example 171 | Example 172 | Example 173 | Example 174 | Example 175 | Example 176 | Example 177 |
| benzimidazole-O-alkyl | Example 178 | Example 179 | Example 180 | Example 181 | Example 182 | Example 183 | Example 184 | Example 185 |
| benzoxazolone-O-alkyl | Example 186 | Example 187 | Example 188 | Example 189 | Example 190 | Example 191 | Example 192 | Example 193 |
| benzoxazolone-O-alkyl (isomer) | Example 194 | Example 195 | Example 196 | Example 197 | Example 198 | Example 199 | Example 200 | Example 201 |

Example 202

4-(3-[N-(2-[4-(5-carbamoyl-2-pyridyloxy) phenyl]-1,1-dimethylethyl)amino]-2-hydroxypropoxy)-2-indolecarboxamide

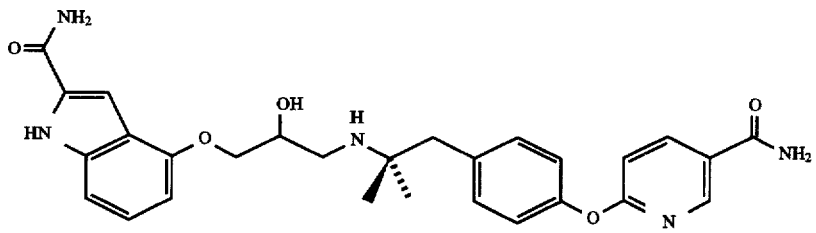

4-(oxiranylmethoxy)-1H-indole-2-carboxamide, (2:1 with dioxane) (0.304 g, 0.36 mmol, 1 eq) and the product of Preparation 40 (0.312 g, 1.09 mmol, 3 eq) were suspended in absolute ethanol (15 mL). The suspension was heated to 50° C. at which time all of the reagents went into solution and heating was continued for 12 hours. Upon completion of the reaction, the mixture was cooled to room temperature and crystals slowly formed. The white solid was filtered and dried under reduced pressure to provide 0.190 g (100% yield) of product.

Anal calcd for $C_{28}H_{31}N_5O_5$; C, 64.97; H, 6.04; N, 13.53: Found; C, 64.79; H, 6.08; N, 13.27; MS: m/z (%) =517.9 (100%), 290.1 (73%), 227.0 (38%).

Example 203

(S)-4-(3-[N-(2-[4-(4-carbamoylphenoxy)phenyl]-1,1-dimethylethyl)amino]-2-hydroxypropoxy)indole

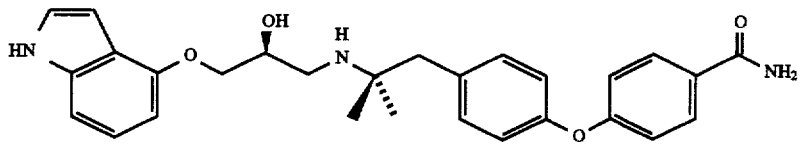

A stirred mixture of (S)-(+)-(oxiranylmethoxy)-1-indole (7.00 g, 37.0 mmol) and 4-(4-(2-amino-2-methylpropyl)-phenoxy)benzamide (21.0 g, 73.8 mmol) in methanol (260 mL) was heated to 45° C. for 22 hours. The mixture was then heated an additional 4 hours at 60° C. The reaction mixture was concentrated in vacuo to an oily residue. The residue was partitioned with ethyl acetate (200 mL), water (35 mL), and 1N HCl (33 mL). The organic solution was washed two times with a solution of 1N HCl (2 mL) in water (33 mL). The ethyl acetate solution was dried with $Na_2SO_4$, filtered, and the filtrate was concentrated in vacuo to a foamy pale yellow residue. The crude product was purified by flash chromatography with 400 g 230–400 mesh silica gel and ethyl acetate:ethanol (5:1 to 4:1 gradient). Concentration of the appropriate fractions afforded 14.8 g (84.5%) of the desired product as a white foamy solid. $^1$H NMR (DMSO-$d_6$) was consistent with the desired product.

Example 204

(S)-4-(3-[N-(2-[4-(4-carbamoylphenoxy) phenyl]-1,1-dimethylethyl)amino]-2-hydroxypropoxy)indole hydrochloride salt

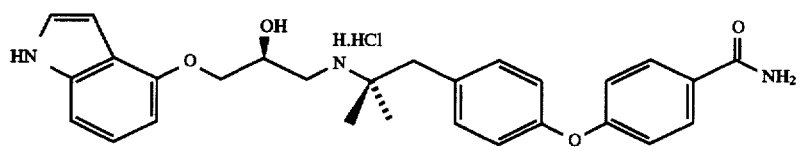

A stirred solution of the product of Example 203 (11.48 g, 24.24 mmol) in ethyl acetate (150 mL) was treated by slow addition with of a 1M HCl/ethyl acetate (24 mL, 24 mmol) solution at ambient temperature. An additional EtOAc (50 mL) was added to the resulting white precipitate, and the slurry was stirred approximately 1 hour at ambient temperature. The product slurry was pressure filtered through a stainless steel filter under nitrogen. The collected product was kept under a steady nitrogen purge for approx. 2 hrs. The filter was then placed in a vacuum oven overnight at 60° C. The product was dried to constant weight in a drying oven at 75° C. to afford 10.38 g (84.1%) as a white solid.

$^1$H NMR (DMSO-$d_6$): δ1.22 (s, 6H), δ2.8–3.5 (m, 5H), δ4.05–4.35 (m, 3H), δ6.45–6.55 (m, 2H), δ6.95–7.40 (m, 6H), δ7.15–7.40 (m, 4H), δ7.85–8.05 (m, 3H), δ11.10 (br. s, 1H); EA: Calculated for $C_{28}H_{32}ClN_3O_4$: C 65.94, H 6.32, N 8.24; Found: C 65.72, H 6.25, N 7.97.

Example 205

(S)-4-(3-[N-(2-[4-(5-carbamoyl-2-pyridyloxy)phenyl]-1,1-dimethylethyl)amino]-2-hydroxypropoxy)indole hydrochloride salt

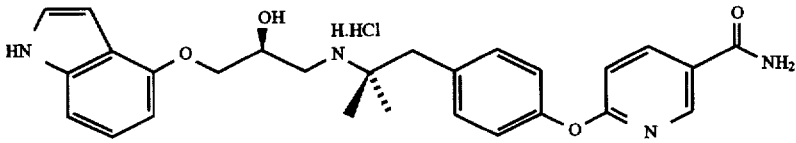

A mixture of 4-(2-amino-2-methylpropyl)phenoxy)-5-carboxamidepyridine (21.11 g, 74.00 mmol), (S)-(+)-4-(oxiranylmethoxy)-1-indole (7.00 g, 37.00 mmol), HOAc (90.4 mg, 1.48 mmol), and water (12 mL) in MeOH (260 mL) was stirred at 60° C. for 19.25 hours. The mixture was cooled and concentrated in vacuo to an oil. The residue was dissolved in EtOAc (185 ml) and water (75 mL) and the resulting layers were separated. The organic layer was extracted with solutions of 1N HCl (34 mL), 1N HCl/MeOH (30 mL/5 mL), 1N HCl/water/MeOH (15 mL/20 mL/10 mL), and 1N HCl (10 mL). The combined acidic aqueous extracts (containing excess starting amine and product) were washed with EtOAc (40 mL). The organic layers were combined and discarded. The pH of the aqueous layer was made slightly basic (pH 7.0–7.5) with the addition of 5N NaOH (10 mL) and 1HCl (1 mL). The aqueous layer was then extracted with EtOAc (100 mL, 2 ×50 mL). The pH of the aqueous layer was raised slightly with the addition of 5N NaOH (0.25 mL). The aqueous layer was diluted with water (5 mL) and MeOH (5 mL) and then was extracted with EtOAc (2×50 mL). The pH of the aqueous layer was raised with 5N NaOH (1 mL) and the layer was extracted with more EtOAc (2×50 mL). The pH of the aqueous layer was again raised with the addition of 5N NaOH (1 mL) and the layer was again extracted with EtOAc (2×50 mL). The combined organic extracts of the basic aqueous layer were concentrated in vacuo to approximately 300 mL. The organic layer was washed with water (50 mL) and then was concentrated in vacuo to 16.64 g of an oil. Purification of 16.31 g of the oil by flash chromatography over 230–400 mesh silica gel using 25:4:0.1 chloroform/methanol/~28% ammonia as an eluent yielded 13.35 g (76.02%) of the free base as product. $^1$H NMR (DMSO-$d_6$) was consistent with the desired product. A stirred solution of the free base (11.86 g, 25.00 mmol) in EtOAc (280 mL) and isopropanol (20 mL) was made acidic with the dropwise addition of 34 mL (approx. 25 mmol HCl) of an approximately 0.725M HCl(g) in EtOAc solution. The resulting slurry was stirred for 2 hours at ambient temperature. The mixture was filtered (nitrogen pressure). The filter cake was washed twice with EtOAc (2×20 mL) and dried in vacuo at 50° C. to yield 12.48 g (97.65%) of a white powder. $^1$H NMR was consistent with the desired product and showed small amounts of EtOAc, IPA, and water):

$^1$H NMR (500 MHz, DMSO-$d_6$): δ11.14 (s, 1H), 9.1 (br s, 1H), 8.7 (br s, 1H), 8.64 (d, 1H), 8.29–8.27 (m, 1H), 8.08 (s, 1H), 7.50 (s, 1H), 7.30–7.29 (d, 2H), 7.24–7.23 (m, 1H), 7.14–6.99 (m, 5H), 6.54–6.49 (m, 2H), 5.93 (br s, 1H), 4.33 (m, 1H), 4.19–4.11 (m, 2H), 3.35 (m, 1), 3.14 (m, 1H), 3.04 (m, 2H), 1.27 (s, 6H); MS (FD+) m/z 949 (31%), 475 (100%).

Example 206

(S)-4-(3-[N-(2-[4-(4-carbamoylphenoxy)phenyl]-1,1-dimethylethyl)amino]-2-hydroxypropoxy)benzotriazole

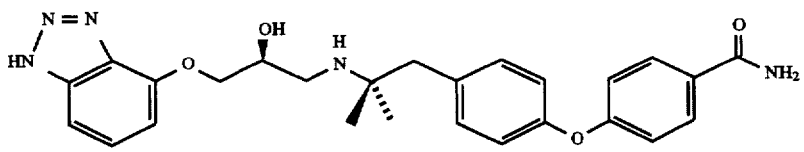

The diamino product from preparation 20 (0.304 g, 0.65 mmol) was dissolved in glacial acetic acid (10 mL) and treated with a solution of sodium nitrite (0.047 g, 0.68 mmol) in water (5 mL) all at once. The reaction was stirred for 5 min and then evaporated to dryness. The resulting residue was purified using column chromatography eluting with 20% MeOH/CHCl3 to provide 0.27 g (87%) as a solid.

MS: m/z (%) =475.9 (100%), 249.0 (5%), 950.7 (5%); $^1$H NMR (300 MHz, d-MeOH): δ1.35 (6H, s); 3.03 (2H, s); 3.40 (2H, m); 4.35 (3H, m); 6.95 (1, d); 7.02 (4H, m); 7.31 (2H, d); 7.38 (2H, d); 7.87 (3H, d).

Example 207

(S)-4-(3-[N-(3-[4-carbamoylphenyl]-1,1-dimethylpropyl)amino]-2-hydroxypropoxy)benzotriazole

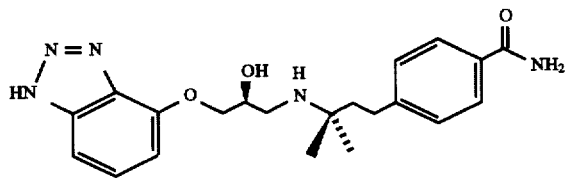

The above titled compound, 0.086 g (63%) was obtained by a procedure described in Example 206 starting from 0.113 g of the appropriate diamine.

MS: m/z (%): 398.3 (100%); 796.1 (20%); $^1$H NMR (300 MHz, d-MeOH): d 1.3 (6H, s); 1.85 (2H, m); 2.65 (2H, m); 3.02 (2H, m); 4.2 (3H, m); 6.72 (1, d); 7.20 (1, d); 7.25 (2H, d); 7.35 (1, d); 7.75 (2H, d).

Example 208

(S)-4-(3-[N-(3-[4-(4-carbamoylphenoxy)phenyl]-1,1-dimethylpropyl)amino]-2-hydroxypropoxy)benzotriazole

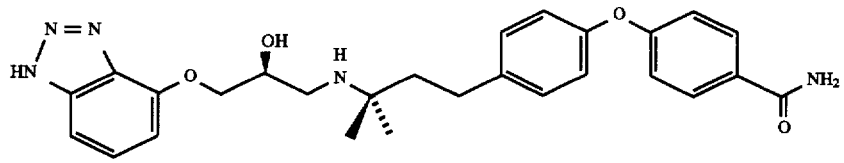

The above titled compound, 0.163 g (69%) was obtained by a procedure described in Example 206 starting from 0.231 g of the appropriate diamine.

MS: m/z (%): 490.0 (100%, m$^+$+1); $^1$H NMR (300 MHz, d-MeOH): d 1.42 (6H, s); 1.98 (2H, m); 2.70 (2H, m); 3.20 (2H, m); 4.30 (3H, s); 6.80 (1, m); 6.98 (4H, m); 7.25 (2H, d); 7.35 (2H, d); 7.85 (2H, d).

Example 209

(S)-4-(3-[N-(2-[4-(5-carbamoyl-2-pyridyloxy)phenyl]-1,1-dimethylethyl)amino]-2-hydroxypropoxy)benzotriazole

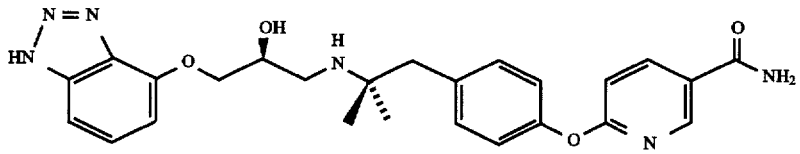

The above titled compound, 0.156 g (65%) was obtained by a procedure described in Example 206 starting from 0.235 g of the appropriate diamine.

MS: m/z (%): 477.0 (100%, m$^+$+1); $^1$H NMR (300 MHz, d-MeOH): d 1.21 (6H, s); 2.90 (2H, s); 3.15 (2H, m); 4.25 (3H, m); 6.79 (1H, d); 7.0 (3H, m); 7.3 (4H, m); 8.25 (1H, d); 8.6 (1, s).

Example 210

(S)-4-(3-[N-(2-[4-([4-methoxycarbonylphenyl]methoxy)phenyl]-1,1-dimethylethyl)amino]-2-hydroxypropoxy)benzotriazole

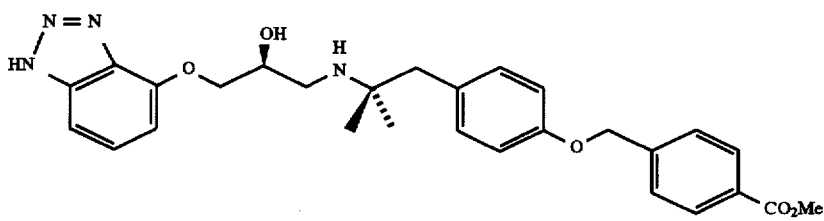

The above titled compound, 0.093 g (65%) was obtained by a procedure described in Example 206 starting from 0.109 g of the appropriate diamine.

MS: m/z (%): 505.1 (100%, m$^+$+1); $^1$H NMR (300 MHz, d-MeOH): 1.3 (6H, s); 2.95 (2H, s); 3.25 (2H, m); 3.95 (3H, s); 4.30 (3H, m); 5.16 (2H, s); 6.85 (1H, d); 6.90 (2H, d); 7.20 (2H, d); 7.40 (2H, m); 7.60 (2H, d); 8.15 (2H, d).

71

Example 211

(S)-4-(3-[N-(3-[4-(N-benzylcarbamoyl)phenyl]-1,1-
dimethylpropyl)amino]-2-hydroxypropoxy)
benzotriazole

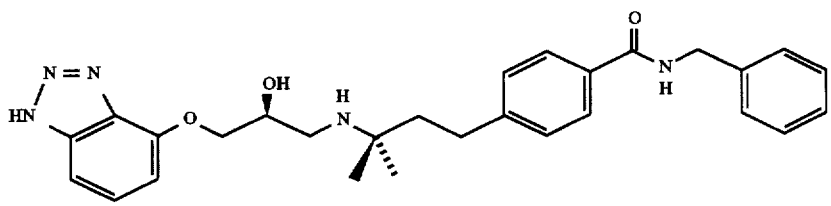

The above titled compound, 0.160 g (63%) was obtained by a procedure described in Example 206 starting from 0.211 g of the appropriate diamine.

MS: m/z (%): 488 (100%, m$^+$+1); $^1$H NMR (300 MHz, d-MeOH): 1.45 (6H, s); 2.0 (2H, m); 2.8 (2H, m); 3.25 (2H, m); 4.35 (3H, s); 4.6 (2H, s); 6.85 (1, m); 7.25 (1, m); 7.35 (8H, m); 7.80 (2H, d).

Example 212

(S)-4-(3-[N-(2-[4-(4-carbamoylphenoxy)phenyl]-1,
1-dimethylethyl)amino]-2-hydroxypropoxy)-2-oxo-
2,3-1H-benzoimidazole hydrochloride salt

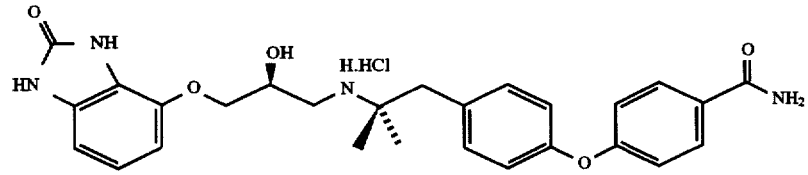

Crude 4-(4-(2-(N-((2S)-3-(2,3-diaminophenoxy)-2-hydroxy propyl)amino)-2-methylpropyl)phenoxy)benzamide (1.49 g, 3.2 mmol) from Preparation 20 was dissolved in 1N HCl (100 mL). Toluene (100 mL) was added and the biphasic mixture treated with triphosgene (4.7 g, 16 mmol) and stirred vigorously for 18 h. A gum precipitated on the sides of the reaction vessel during the course of the reaction. The liquid was decanted off and the gum dissolved in MeOH. The solution was absorbed on silica and chromatographed on 200 g of silica eluting with EtOAc/water/n-propanol (80 vol/15 vol/5 vol, shake and use top layer) to remove the starting material. The column was then eluted with CHCl$_3$/MeOH/NH$_4$OH (25 vol/5 vol/1 vol) to obtain the product. After concentrating and azeotroping with EtOH there was obtained 715 mg (46%) of a white foam. MS. $^1$H NMR (DMSO-d$_6$) consistent with desired product.

The free base (528 mg, 1.08 mmol) prepared above was dissolved in EtOH and treated with 4N HCl in dioxane (0.75 mL, 3.0 mmol). The solution was concentrated in vacuo to provide 595 mg of a white foam as the hydrochloride salt. MS. $^1$H NMR (DMSO-d$_6$) consistent with desired product.

As previously noted, the compounds of the present invention are potent, selective β$_3$ adrenergic receptor agonists. This pharmacological activity was determined in the functional agonist β$_3$ assay.

72

Functional Agonists

β$_3$ Assay

Cell Lines The hβ$_2$ DNA was expressed from a plasmid 57537 obtained from American Type Culture Collection. hβ$_1$ and hβ$_3$ adrenergic receptors were cloned from human genomic libraries using the polymerase chain reaction method with degenerate probes. Full length receptors were cloned, expressed and sequenced to verify identity according to published sequences (hβ$_1$: T. Frielle et. al. (1993) Molecular Pharmacology 44: 264–270). These receptors were then expressed in the DXB-11 variant of CHO cells using a vector restoring tetrahydrofolate reductase and hygromycin resistance. Rat β$_3$ receptor expressing CHO cell line is known in the art. Mol. Pharm., Vol 40,pp. 895–99 (1991). CHO cells were grown in 10% dialyzed FBS./high glucose DMEM/0.1% proline.

cAMP Assay Cell membranes were harvested from the above cell line using hypotonic 25 mM Hepes (pH 7.4), 1 MM EDTA, 20 μg/mL leupeptin, 1 mM PMSF buffer with scraping followed by differential centrifugation. Membranes were incubated in 25 mM Tris (pH 7.6), 0.2% BSA, 2.6 mM Mg, 0.8 mM ATP, 0.1 mM GTP, 5 mM creatine phosphate, creatine kinase 50 U/mL, 0.2 mM IBMX at 32° C. Agonists were added and incubation continued for 15 m. cAMP produced was assayed using a fluorescent tracer-immuno assay method.

Intact cell assays were performed using suspended cells removed from culture flasks by trypsin treatment. Cells were preincubated with 0.5 mM IBMX at 37° C. Agonists were added and incubation continued for 15 m. Incubation was stopped by heating suspension in boiling water. cAMP or cGMP in these and the soleus incubations were assayed by RIA (Amersham).

The compounds of the invention are agonists of the β$_3$ receptor. Isoproterenol is accepted in the art as a non-selective β$_3$ agonist and is widely used as a comparator in evaluating the activity of compounds. See Trends in Pharm. Sci. 15: 3 (1994). In the Functional Agonist β$_3$ assay, the compounds demonstrated at least 30%, preferably 50% and most preferably over 85% of isoproterenolls response at a single dose of 50βmol. Dose response titrations on the agonists described reveal EC$_{50}$ values of <10 βM, preferably <1mmol. In the functional assay, dose titration furnishes an EC$_{50}$ for isoproterenol of 1.1±0.5 βM.

When screened against the μ$_1$ and μ$_2$ receptors in the functional assay, dose titration experiments indicate that greatly reduced or no receptor stimulation is observed with the compounds of the invention. This is defined by measuring the intrinsic activity (maximal response achieved) as compared to isoproterenol. The claimed compounds of Formula I are selective $\beta_3$ receptor agonists and have an intrinsic activity of <3% of isoproterenol's response.

Thus, the compounds of the invention are selective $\beta_3$ adrenergic receptor agonists.

As agonists of $\beta_3$, the compounds are useful in treating conditions in a mammal in which the $\beta_3$ receptor has been demonstrated to play a role. The prefered mammal of treatment is a human. The relationship between modulating the $\beta_3$ receptor and treatment of diseases, such Type II diabetes and obesity, is well established in the art. Other conditions recognized in the art include: gastrointestinal disorders such as gastrointestinal motility, asthma, and depression. Thus, the present compounds are useful in the treatment of inflammatory bowel disease (Crohn's disease or ulcerative colitis), irritable bowel syndrome, non-specific diarrhoea dumping syndrome, asthma, and depression.

In treating non-human mammals, the compounds of the present invention are useful for increasing weight gain and/or improving the feed utilization efficiency and/or increasing lean body mass and/or decreasing birth mortality rate and increasing post/natal survival rate.

The compounds of Formulas I and II are preferably formulated prior to administration. Therefore, yet another embodiment of the present invention is a pharmaceutical formulation comprising a compound of Formula I or II and one or more pharmaceutically acceptable carriers, diluents or excipients.

The present pharmaceutical formulations are prepared by known procedures using well-known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions are preferably formulated in a unit dosage form, each dosage containing from about 0.1 to about 500 mg, preferably about 5 to about 200 mg, of the active ingredient. However, it will be understood that the therapeutic dosage administered will be determined by the physician in the light of the relevant circumstances including the condition to be treated, the choice of compound to be administered and the chosen route of administration, and therefore, the above dosage ranges are not intended to limit the scope of the invention in any way. The compounds can be administered by a variety of routes including the oral, rectal, transdermal, subcutaneous, topical, intravenous, intramuscular or intranasal routes. For all indications, a typical daily dose will contain from about 0.05 mg/kg to about 20 mg/kg of the active compound of this invention. Preferred daily doses will be about 0.1 to about 10 mg/kg, ideally about 0.1 to about 5 mg/kg. However, for topical administration a typical dosage is about 1 to about 500 µg compound per cm$^2$ of an affected tissue. Preferably, the applied amount of compound will range from about 30 to about 300 µg/cm$^2$, more preferably, from about 50 to about 200 µg/cm$^2$, and, most preferably, from about 60 to about 100 µg/cm$^2$.

The following formulation examples are illustrative only and are not intended to limit the scope of the invention in any way.

Formulation 1

Hard gelatin capsules are prepared using the following ingredients:

|  | Quantity (mg/capsule) |
| --- | --- |
| (S)-4-(3-[N-(2-[4-(4-carbamoylphenoxy)phenyl]-1,1-dimethylethyl)amino]-2-hydroxypropoxy)indole hydrochloride salt | 25 |
| starch, dried | 425 |
| magnesium stearate | 10 |
| Total | 460 mg |

The above ingredients are mixed and filled into hard gelatin capsules in 460 mg quantities.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

We claim:

1. A compound of the formula:

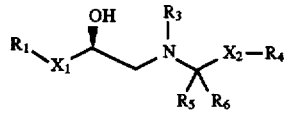

wherein:

$R_1$ is

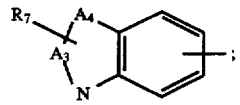

the bond between $A_3$ and $A_4$ is either a single or double bond;

$A_3$ and $A_4$ are independently carbon or nitrogen;

$R_7$ is hydrogen, halo, hydroxy, $C_1$-$C_4$ alkyl, $C_1$-$C_4$ haloalkyl, aryl, CN, COOR$_2$, CONHR$_2$, NHCOR$_2$, OR$_2$, NHR$_2$, SR$_2$, SO$_2$R$_2$, SO$_2$NHR$_2$, or SOR$_2$;

$R_2$ and $R_3$ are independently hydrogen, $C_1-C_4$ alkyl, or aryl;

$X_1$ is $-OHC_2-$, $-SCH_2-$, or a bond;

$R_4$ is an optionally substituted heterocycle or a moiety of the structure

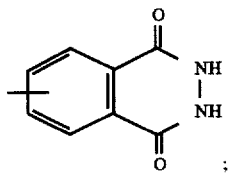

$X_2$ is a bond, or a 1 to 5 carbon straight or branched alkylene;

$R_5$ is hydrogen or $C_1-C_4$ alkyl;

$R_6$ is hydrogen or $C_1-C_4$ alkyl;

or $R_5$ and $R_6$ combine with the carbon to which each is attached to form a $C_3-C_6$ cycloalkyl;

or $R_6$ combines with $X_2$ and the carbon to which each is attached to form a $C_3-C_8$ cycloalkyl;

or pharmaceutically acceptable salts thereof.

2. The compound of claim 1 wherein $A_3$ and $A_4$ are carbon and the bond between $A_3$ and $A_4$ is a double bond.

3. The compound of claim 2 wherein $R_4$ is

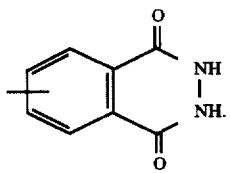

4. The compound of claim 3 wherein $R_3$ is hydrogen, $R_5$ is $C_1-C_4$ alkyl, $R_6$ is $C_1-C_4$ alkyl, and $R_7$ is hydrogen.

5. The compound of claim 4 wherein $R_5$ is methyl and $R_6$ is methyl.

6. The compound of claim 1 wherein $A_3$ is nitrogen, $A_4$ is nitrogen, and the bond between $A_3$ and $A_4$ is a double bond.

7. The compound of claim 6 wherein $R_3$ is hydrogen, $R_5$ is $C_1-C_4$ alkyl, $R_6$ is $C_1-C_4$ alkyl, and $R_7$ is hydrogen.

8. The compound of claim 7 wherein $R_5$ is methyl and $R_6$ is methyl.

9. A pharmaceutical formulation comprising as an active ingredient a compound of claim 1 with one or more pharmaceutically acceptable carriers, excipients, or diluents.

10. A pharmaceutical formulation comprising as an active ingredient a compound of claim 5 with one or more pharmaceutically acceptable carriers, excipients, or diluents.

11. A pharmaceutical formulation comprising as an active ingredient a compound of claim 8 with one or more pharmaceutically acceptable carriers, excipients, or diluents.

12. A method of agonizing the $\beta_3$ receptor which comprises administering to a mammal in need thereof a compound of claim 1.

13. A method of agonizing the $\beta_3$ receptor which comprises administering to a mammal in need thereof a compound of claim 5.

14. A method of agonizing the $\beta_3$ receptor which comprises administering to a mammal in need thereof a compound of claim 8.

15. A method of treating Type II Diabetes which comprises administering to a mammal in need thereof a compound of claim 1.

16. A method of treating Type II Diabetes which comprises administering to a mammal in need thereof a compound of claim 5.

17. A method of treating Type II Diabetes which comprises administering to a mammal in need thereof a compound of claim 8.

18. A method of treating obesity which comprises administering to a mammal in need thereof a compound of claim 1.

19. A method of treating obesity which comprises administering to a mammal in need thereof a compound of claim 5.

20. A method of treating obesity which comprises administering to a mammal in need thereof a compound of claim 8.

* * * * *